(12) United States Patent
Fritz

(10) Patent No.: US 11,744,744 B2
(45) Date of Patent: *Sep. 5, 2023

(54) CURVED ELASTIC WITH ENTRAPMENT

(71) Applicant: Curt G. Joa, Inc., Sheboygan Falls, WI (US)

(72) Inventor: Jeffrey W. Fritz, Plymouth, WI (US)

(73) Assignee: CURT G. JOA, INC., Sheboygan Falls, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/454,855

(22) Filed: Nov. 15, 2021

(65) Prior Publication Data
US 2022/0071809 A1    Mar. 10, 2022

Related U.S. Application Data

(63) Continuation of application No. 16/947,779, filed on Aug. 17, 2020, now Pat. No. 11,173,072.
(Continued)

(51) Int. Cl.
*B29C 65/08* (2006.01)
*A61F 13/15* (2006.01)
(Continued)

(52) U.S. Cl.
CPC ...... *A61F 13/15593* (2013.01); *B29C 65/086* (2013.01); *B29C 65/087* (2013.01);
(Continued)

(58) Field of Classification Search
CPC ............. B29C 65/086; B29C 66/83411; B29C 66/83511
(Continued)

(56) References Cited

U.S. PATENT DOCUMENTS 3,580,783 A    5/1971   Glaze
3,622,434 A   11/1971   Newman
(Continued)

FOREIGN PATENT DOCUMENTS

CN    101868210 B    9/2014
EP     0274752 A3    5/1990
(Continued)

OTHER PUBLICATIONS

Machine Translation for JP2014198179 (A).
(Continued)

*Primary Examiner* — James D Sells
(74) *Attorney, Agent, or Firm* — Klintworth & Rozenblat IP LLP

(57) ABSTRACT

An apparatus for manufacturing an elastic composite structure is provided. The apparatus includes an anvil having a face with a first edge and a second edge separated in a cross-machine direction and a first contact surface extending out from the face, the first contact surface including a first notch. The first notch has an interior configured to receive a portion of an elastic thread and a portion of a web layer therein, and the first notch includes a first facing surface and a second facing surface defining at least a portion of the interior. Each of the first facing surface and the second facing surface are in a non-perpendicular orientation relative to the first contact surface and angled toward the first edge of the face.

20 Claims, 9 Drawing Sheets

Related U.S. Application Data

(60) Provisional application No. 62/896,063, filed on Sep. 5, 2019.

(51) Int. Cl.
*B29C 65/00* (2006.01)
*B29L 31/48* (2006.01)

(52) U.S. Cl.
CPC ...... *B29C 66/729* (2013.01); *B29C 66/83411* (2013.01); *B29C 66/83511* (2013.01); *B29L 2031/4878* (2013.01)

(58) Field of Classification Search
USPC ...................................................... 156/580.1
See application file for complete search history.

(56) References Cited

U.S. PATENT DOCUMENTS

| | | |
|---|---|---|
| 3,658,064 A | 4/1972 | Pociluyko |
| 3,668,054 A | 6/1972 | Stumpf |
| 3,844,869 A | 10/1974 | Rust, Jr. |
| 3,884,227 A | 5/1975 | Lutz et al. |
| 3,982,988 A | 9/1976 | Heimberger |
| 3,993,532 A | 11/1976 | McDonald et al. |
| 4,088,731 A | 5/1978 | Groome |
| 4,305,988 A | 12/1981 | Kocher |
| 4,305,998 A | 12/1981 | Manty |
| 4,333,978 A | 6/1982 | Kocher |
| 4,336,203 A | 6/1982 | Zucker et al. |
| 4,485,819 A | 12/1984 | Igl |
| 4,662,005 A | 5/1987 | Grier-Idris |
| 4,770,656 A | 9/1988 | Proxmire et al. |
| 4,808,176 A | 2/1989 | Kielpikowski |
| 4,833,734 A | 5/1989 | Der Estephanian |
| 4,834,738 A | 5/1989 | Kielpikowski et al. |
| 4,842,596 A | 6/1989 | Kielpikowski et al. |
| 4,863,542 A | 9/1989 | Oshefsky et al. |
| 4,919,738 A | 4/1990 | Ball et al. |
| 5,094,717 A | 3/1992 | Manning et al. |
| 5,163,932 A | 11/1992 | Nomura et al. |
| 5,353,798 A | 10/1994 | Sieben |
| 5,468,320 A | 11/1995 | Zafiroglu |
| 5,530,979 A | 7/1996 | Whitley |
| 5,561,863 A | 10/1996 | Carlson, II |
| 5,618,378 A | 4/1997 | Cahill |
| 5,624,420 A | 4/1997 | Bridges et al. |
| 5,643,396 A | 7/1997 | Rajala et al. |
| 5,660,657 A | 8/1997 | Rajala et al. |
| 5,694,925 A | 12/1997 | Reese et al. |
| 5,699,791 A | 12/1997 | Sukiennik et al. |
| 5,707,470 A | 1/1998 | Rajala et al. |
| 5,711,847 A | 1/1998 | Rajala et al. |
| 5,745,922 A | 5/1998 | Rajala et al. |
| 5,769,993 A | 6/1998 | Baldauf |
| 5,789,065 A | 8/1998 | Haffner et al. |
| 5,797,895 A | 8/1998 | Widlund et al. |
| 5,803,075 A | 9/1998 | Yavitz |
| 5,813,398 A | 9/1998 | Baird et al. |
| 5,817,584 A | 10/1998 | Singer et al. |
| 5,883,026 A | 3/1999 | Reader et al. |
| 5,934,275 A | 8/1999 | Gazzara |
| 5,954,055 A | 9/1999 | Miyake |
| D424,688 S | 5/2000 | Bryant et al. |
| 6,055,982 A | 5/2000 | Brunson et al. |
| 6,057,024 A | 5/2000 | Mleziva et al. |
| 6,062,220 A | 5/2000 | Whitaker et al. |
| 6,123,077 A | 9/2000 | Bostock et al. |
| 6,125,849 A | 10/2000 | Williams et al. |
| 6,165,298 A | 12/2000 | Samida et al. |
| 6,173,712 B1 | 1/2001 | Brunson |
| 6,197,404 B1 | 3/2001 | Varona |
| 6,213,125 B1 | 4/2001 | Reese et al. |
| 6,217,889 B1 | 4/2001 | Lorenzi et al. |
| 6,235,137 B1 | 5/2001 | Eperen et al. |
| 6,257,235 B1 | 7/2001 | Bowen |
| 6,279,570 B1 | 8/2001 | Mittelstadt et al. |
| 6,291,039 B1 | 9/2001 | Combe et al. |
| 6,295,714 B1 | 10/2001 | Roychowdhury et al. |
| 6,332,465 B1 | 12/2001 | Xue et al. |
| 6,340,782 B1 | 1/2002 | Kling et al. |
| 6,354,296 B1 | 3/2002 | Baumann et al. |
| 6,394,090 B1 | 5/2002 | Chen et al. |
| 6,427,693 B1 | 8/2002 | Blackstock et al. |
| 6,460,539 B1 | 10/2002 | Japuntich et al. |
| 6,482,278 B1 | 11/2002 | McCabe et al. |
| 6,484,722 B2 | 11/2002 | Bostock et al. |
| 6,506,474 B2 | 1/2003 | Tsuji |
| 6,534,694 B2 | 3/2003 | Kling et al. |
| 6,536,434 B1 | 3/2003 | Bostock et al. |
| 6,541,679 B2 | 4/2003 | Betrabet et al. |
| 6,568,392 B1 | 5/2003 | Bostock et al. |
| 6,584,976 B2 | 7/2003 | Japuntich et al. |
| 6,604,524 B1 | 8/2003 | Curran et al. |
| 6,613,955 B1 | 9/2003 | Lindsay et al. |
| 6,623,837 B2 | 9/2003 | Morman et al. |
| 6,644,314 B1 | 11/2003 | Elsberg |
| 6,652,693 B2 | 11/2003 | Burriss et al. |
| 6,673,980 B1 | 1/2004 | Varona et al. |
| 6,712,922 B2 | 3/2004 | Sorenson et al. |
| 6,715,489 B2 | 4/2004 | Bostock et al. |
| 6,722,366 B2 | 4/2004 | Bostock et al. |
| 6,730,188 B2 | 5/2004 | Sanders |
| 6,761,710 B2 | 7/2004 | D'Acchioli et al. |
| 6,780,263 B2 | 8/2004 | Delisle |
| 6,843,872 B2 | 1/2005 | Morman |
| 6,886,563 B2 | 5/2005 | Bostock et al. |
| 6,889,622 B2 | 5/2005 | Marcangelo |
| 6,914,018 B1 | 7/2005 | Uitenbroek et al. |
| 6,928,657 B2 | 8/2005 | Bell et al. |
| 6,953,452 B2 | 10/2005 | Popp et al. |
| 7,008,496 B2 | 3/2006 | Morman |
| 7,021,227 B2 | 4/2006 | Marcangelo |
| 7,025,841 B2 | 4/2006 | Owen |
| 7,044,131 B2 | 5/2006 | Griesbach et al. |
| 7,069,930 B2 | 7/2006 | Bostock et al. |
| 7,118,558 B2 | 10/2006 | Wu et al. |
| 7,198,688 B2 | 4/2007 | Mortell et al. |
| 7,211,531 B2 | 5/2007 | Schneider et al. |
| 7,217,261 B2 | 5/2007 | Otsubo et al. |
| 7,290,545 B2 | 11/2007 | Kleman et al. |
| 7,316,840 B2 | 1/2008 | Neculescu et al. |
| 7,361,241 B2 | 4/2008 | Barth et al. |
| 7,378,566 B2 | 5/2008 | Soerens et al. |
| 7,469,427 B2 | 12/2008 | Yang et al. |
| 7,507,680 B2 | 3/2009 | Middlesworth et al. |
| 7,582,348 B2 | 9/2009 | Ando et al. |
| 7,617,787 B2 | 11/2009 | Marcangelo |
| 7,619,167 B2 | 11/2009 | Lee et al. |
| 7,638,014 B2 | 12/2009 | Coose et al. |
| 7,642,398 B2 | 1/2010 | Jarpenberg et al. |
| 7,691,138 B2 | 4/2010 | Stenzel et al. |
| 7,708,849 B2 | 5/2010 | McCabe |
| 7,722,734 B2 | 5/2010 | Otsubo |
| 7,725,948 B2 | 6/2010 | Steindorf |
| 7,799,967 B2 | 9/2010 | Ranganathan et al. |
| 7,833,369 B2 | 11/2010 | Zhou et al. |
| 7,845,351 B2 | 12/2010 | Mathis et al. |
| 7,861,756 B2 | 1/2011 | Jenquin et al. |
| 7,901,392 B2 | 3/2011 | Kline et al. |
| 7,955,418 B2 | 6/2011 | Claussen et al. |
| 7,981,231 B2 | 7/2011 | Schneider et al. |
| 8,007,484 B2 | 8/2011 | McCabe et al. |
| 8,074,660 B2 | 12/2011 | Duffy |
| 8,075,543 B2 | 12/2011 | Okuda |
| 8,091,550 B2 | 1/2012 | Steindorf |
| 8,109,916 B2 | 2/2012 | Wennerback |
| 8,142,411 B2 | 3/2012 | Kline et al. |
| 8,146,594 B2 | 4/2012 | Bostock et al. |
| 8,182,624 B2 | 5/2012 | Handziak |
| 8,207,395 B2 | 6/2012 | Soerens et al. |
| 8,268,444 B2 | 9/2012 | Okaya |
| 8,282,617 B2 | 10/2012 | Kaneda |
| 8,298,205 B2 | 10/2012 | Norrby et al. |

(56) References Cited

U.S. PATENT DOCUMENTS

| | | |
|---|---|---|
| 8,308,706 B2 | 11/2012 | Fukae |
| 8,323,257 B2 | 12/2012 | Melik et al. |
| 8,328,820 B2 | 12/2012 | Diamant et al. |
| 8,360,067 B2 | 1/2013 | Duffy |
| 8,375,950 B2 | 2/2013 | Bostock et al. |
| 8,435,223 B2 | 5/2013 | Roe et al. |
| 8,440,043 B1 | 5/2013 | Schneider et al. |
| 8,470,946 B1 | 6/2013 | Carlson |
| 8,528,560 B2 | 9/2013 | Duffy |
| 8,562,777 B2 | 10/2013 | Drake |
| 8,585,667 B2 | 11/2013 | Roe et al. |
| 8,622,059 B2 | 1/2014 | Kleman |
| 8,640,704 B2 | 2/2014 | Spoo et al. |
| 8,647,319 B2 | 2/2014 | Een et al. |
| 8,652,114 B2 | 2/2014 | Roe et al. |
| 8,652,115 B2 | 2/2014 | Roe et al. |
| 8,669,409 B2 | 3/2014 | Roe |
| 8,741,083 B2 | 6/2014 | Wennerback et al. |
| 8,758,786 B2 | 6/2014 | Hassler |
| 8,771,449 B2 | 7/2014 | Takino et al. |
| 8,784,395 B2 | 7/2014 | Roe et al. |
| 8,784,397 B2 | 7/2014 | Chang et al. |
| 8,808,263 B2 | 8/2014 | Roe et al. |
| 8,881,729 B2 | 11/2014 | Duffy |
| 8,926,579 B2 | 1/2015 | Wang et al. |
| 8,932,273 B2 | 1/2015 | Roe et al. |
| 8,936,586 B2 | 1/2015 | Roe |
| 8,992,497 B2 | 3/2015 | Roe et al. |
| 8,998,870 B2 | 4/2015 | Roe |
| 9,011,402 B2 | 4/2015 | Roe et al. |
| 9,011,404 B2 | 4/2015 | Kobayashi et al. |
| 9,012,013 B2 | 4/2015 | Duffy |
| 9,028,462 B2 | 5/2015 | Poole et al. |
| 9,056,033 B2 | 6/2015 | Fenske |
| 9,060,905 B2 | 6/2015 | Wang et al. |
| 9,078,789 B2 | 7/2015 | Wang et al. |
| 9,078,792 B2 | 7/2015 | Ruiz |
| 9,089,456 B2 | 7/2015 | Roe et al. |
| 9,095,478 B2 | 8/2015 | Roe |
| 9,180,059 B2 | 11/2015 | Roe et al. |
| 9,301,881 B2 | 4/2016 | Ando et al. |
| 9,387,138 B2 | 7/2016 | Roe |
| 9,539,735 B2 | 1/2017 | Ferguson et al. |
| 9,603,395 B2 | 3/2017 | Duffy |
| 9,603,396 B2 | 3/2017 | Duffy |
| 9,615,612 B2 | 4/2017 | Duffy |
| 9,770,057 B2 | 9/2017 | Duffy |
| 9,770,058 B2 | 9/2017 | Angadjivand et al. |
| 9,770,611 B2 | 9/2017 | Facer et al. |
| 9,809,414 B2 | 11/2017 | Fritz et al. |
| 9,868,002 B2 | 1/2018 | Duffy |
| 9,913,764 B2 | 3/2018 | Thomas et al. |
| 10,040,621 B2 | 8/2018 | Duffy et al. |
| 10,130,833 B2 | 11/2018 | Angadjivand et al. |
| 10,137,321 B2 | 11/2018 | Martin |
| 10,143,246 B2 | 12/2018 | Houde et al. |
| D837,970 S | 1/2019 | Henderson et al. |
| 10,182,603 B2 | 1/2019 | Duffy |
| 10,213,348 B2 | 2/2019 | Gualtieri et al. |
| 10,227,202 B2 | 3/2019 | Pamperin et al. |
| 10,259,165 B2 | 4/2019 | Ehlert et al. |
| D848,678 S | 5/2019 | Andrews |
| 10,314,346 B2 | 6/2019 | Potnis et al. |
| 10,457,436 B2 | 10/2019 | Spencer et al. |
| 10,492,547 B2 | 12/2019 | Weber et al. |
| 10,494,221 B2 | 12/2019 | Harris et al. |
| 10,537,479 B2 | 1/2020 | Schuette et al. |
| 10,596,045 B2 | 3/2020 | Koshijima et al. |
| 10,596,047 B2 | 3/2020 | Coenen et al. |
| 10,751,228 B2 | 8/2020 | Kurohara et al. |
| 10,758,428 B2 | 9/2020 | Nakamura et al. |
| 10,786,398 B2 | 9/2020 | Koshijima et al. |
| 10,792,194 B2 | 10/2020 | Hohm et al. |
| 10,889,066 B2 | 1/2021 | Begrow et al. |
| 10,893,986 B2 | 1/2021 | Manabe et al. |
| 10,973,703 B2 | 4/2021 | Coenen et al. |
| 11,020,281 B2 | 6/2021 | Ishikawa |
| 11,020,286 B2 | 6/2021 | Kaufman et al. |
| 11,129,753 B2 | 9/2021 | Schneider et al. |
| 11,141,321 B2 | 10/2021 | Schneider et al. |
| 11,147,717 B2 | 10/2021 | Schneider et al. |
| 11,173,072 B2 * | 11/2021 | Fritz .................... B29C 65/087 |
| 11,191,676 B2 | 12/2021 | Koshijima et al. |
| 11,219,555 B2 | 1/2022 | Schneider et al. |
| 11,254,062 B2 | 2/2022 | Ehlert et al. |
| 11,254,066 B2 | 2/2022 | Begrow et al. |
| 11,399,989 B2 | 8/2022 | Polidori et al. |
| 11,433,620 B2 | 9/2022 | Ehlert et al. |
| 2001/0025683 A1 | 10/2001 | Burriss et al. |
| 2001/0034508 A1 | 10/2001 | Betrabet et al. |
| 2001/0044250 A1 | 11/2001 | Tsuji |
| 2002/0092604 A1 | 7/2002 | McCabe et al. |
| 2002/0116027 A1 | 8/2002 | Egan et al. |
| 2002/0119288 A1 | 8/2002 | Morman et al. |
| 2002/0157778 A1 | 10/2002 | Sorenson et al. |
| 2003/0051803 A1 | 3/2003 | Sanders |
| 2003/0120250 A1 | 6/2003 | Betrabet et al. |
| 2003/0124306 A1 | 7/2003 | Morman |
| 2003/0125706 A1 | 7/2003 | Popp et al. |
| 2003/0125707 A1 | 7/2003 | Popp et al. |
| 2003/0135185 A1 | 7/2003 | Crowther |
| 2003/0144643 A1 | 7/2003 | Jarpenberg et al. |
| 2004/0005832 A1 | 1/2004 | Neculescu et al. |
| 2004/0059280 A1 | 3/2004 | Makower et al. |
| 2004/0112509 A1 | 6/2004 | Morman |
| 2004/0116885 A1 | 6/2004 | Soerens et al. |
| 2004/0127614 A1 | 7/2004 | Jiang et al. |
| 2004/0138635 A1 | 7/2004 | Sorenson et al. |
| 2004/0158217 A1 | 8/2004 | Wu et al. |
| 2004/0192140 A1 | 9/2004 | Schneider et al. |
| 2004/0219854 A1 | 11/2004 | Groitzsch et al. |
| 2004/0226645 A1 | 11/2004 | Owen |
| 2004/0243085 A1 | 12/2004 | Veith et al. |
| 2004/0261230 A1 | 12/2004 | Neeb et al. |
| 2005/0095942 A1 | 5/2005 | Mueller et al. |
| 2005/0101216 A1 | 5/2005 | Middlesworth et al. |
| 2005/0131374 A1 | 6/2005 | Otsubo et al. |
| 2005/0142331 A1 | 6/2005 | Anderson et al. |
| 2005/0148261 A1 | 7/2005 | Close et al. |
| 2005/0176029 A1 | 8/2005 | Heller et al. |
| 2005/0183646 A1 | 8/2005 | Marcangelo |
| 2005/0216058 A1 | 9/2005 | Egan et al. |
| 2005/0228350 A1 | 10/2005 | Ranganathan et al. |
| 2006/0009104 A1 | 1/2006 | Schneider et al. |
| 2006/0069373 A1 | 3/2006 | Schlinz et al. |
| 2006/0099871 A1 | 5/2006 | Poruthoor et al. |
| 2006/0130964 A1 | 6/2006 | McCabe |
| 2006/0135923 A1 | 6/2006 | Boggs et al. |
| 2006/0135932 A1 | 6/2006 | Abuto et al. |
| 2006/0138693 A1 | 6/2006 | Tuman et al. |
| 2006/0149208 A1 | 7/2006 | Carr |
| 2006/0180068 A1 | 8/2006 | Marcangelo |
| 2006/0224137 A1 | 10/2006 | McCabe et al. |
| 2006/0228969 A1 | 10/2006 | Erdman |
| 2006/0238757 A1 | 10/2006 | Silcott |
| 2006/0270302 A1 | 11/2006 | Ando et al. |
| 2007/0000021 A1 | 1/2007 | Yang et al. |
| 2007/0068529 A1 | 3/2007 | Kalatoor et al. |
| 2007/0131335 A1 | 6/2007 | Zhou et al. |
| 2007/0175477 A1 | 8/2007 | Baggett |
| 2007/0218245 A1 | 9/2007 | Schneider et al. |
| 2007/0286987 A1 | 12/2007 | Anderson et al. |
| 2008/0103460 A1 | 5/2008 | Close et al. |
| 2008/0110554 A1 | 5/2008 | Otsubo |
| 2008/0262455 A1 | 10/2008 | Soerens et al. |
| 2009/0134049 A1 | 5/2009 | Melik et al. |
| 2009/0163940 A1 | 6/2009 | Sliwa |
| 2009/0208703 A1 | 8/2009 | Wennerback et al. |
| 2009/0242098 A1 | 10/2009 | Handziak |
| 2009/0306616 A1 | 12/2009 | Wennerback |
| 2009/0326503 A1 | 12/2009 | Lakso et al. |
| 2009/0326504 A1 | 12/2009 | Kaneda |
| 2010/0015190 A1 | 1/2010 | Hassler |
| 2010/0076390 A1 | 3/2010 | Norrby et al. |

(56) References Cited

U.S. PATENT DOCUMENTS

| | | |
|---|---|---|
| 2010/0076394 A1 | 3/2010 | Hayase et al. |
| 2010/0087352 A1 | 4/2010 | Mason |
| 2010/0286709 A1 | 11/2010 | Diamant et al. |
| 2010/0298798 A1 | 11/2010 | Lakso et al. |
| 2010/0324513 A1 | 12/2010 | Wennerback |
| 2011/0055998 A1 | 3/2011 | Tai et al. |
| 2011/0061786 A1 | 3/2011 | Mason |
| 2011/0067797 A1 | 3/2011 | Schneider et al. |
| 2011/0118689 A1 | 5/2011 | Een et al. |
| 2011/0152811 A1 | 6/2011 | Bing-Wo et al. |
| 2011/0184372 A1 | 7/2011 | Esping Ostlin et al. |
| 2011/0192888 A1 | 8/2011 | Tai et al. |
| 2011/0251576 A1 | 10/2011 | Ando et al. |
| 2011/0257616 A1 | 10/2011 | Lakso et al. |
| 2012/0088103 A1 | 4/2012 | Sugiura et al. |
| 2012/0095429 A1 | 4/2012 | Kobayashi et al. |
| 2012/0123367 A1 | 5/2012 | Melik et al. |
| 2012/0123368 A1 | 5/2012 | Melik et al. |
| 2012/0123369 A1 | 5/2012 | Melik et al. |
| 2012/0123370 A1 | 5/2012 | Melik et al. |
| 2012/0123371 A1 | 5/2012 | Melik et al. |
| 2012/0123372 A1 | 5/2012 | Melik et al. |
| 2012/0123373 A1 | 5/2012 | Melik et al. |
| 2012/0175064 A1 | 7/2012 | Yamamoto |
| 2012/0228988 A1 | 9/2012 | Cutsforth |
| 2012/0321856 A1 | 12/2012 | Afshari |
| 2012/0328841 A1 | 12/2012 | Afshari |
| 2012/0328842 A1 | 12/2012 | Afshari |
| 2013/0011601 A1 | 1/2013 | Fenske |
| 2013/0042411 A1 | 2/2013 | Vitale |
| 2013/0048191 A1 | 2/2013 | Durrance et al. |
| 2013/0079797 A1 | 3/2013 | Diamant et al. |
| 2013/0157012 A1 | 6/2013 | Qin et al. |
| 2013/0165896 A1 | 6/2013 | Carbonari |
| 2013/0255865 A1 | 10/2013 | Brown et al. |
| 2014/0093687 A1 | 4/2014 | Humiston et al. |
| 2014/0099469 A1 | 4/2014 | Abuto et al. |
| 2014/0102650 A1 | 4/2014 | Qin et al. |
| 2014/0180126 A1 | 6/2014 | Millett et al. |
| 2015/0164705 A1 | 6/2015 | Thomas et al. |
| 2016/0058624 A1 | 3/2016 | Hohm et al. |
| 2016/0228305 A1 | 8/2016 | Gualtieri et al. |
| 2016/0288407 A1 | 10/2016 | Ehlert et al. |
| 2016/0331600 A1 | 11/2016 | Polidori et al. |
| 2017/0113366 A1 | 4/2017 | Ferguson et al. |
| 2017/0281417 A1 | 10/2017 | Ishikawa |
| 2018/0027899 A1 | 2/2018 | Facer et al. |
| 2018/0042788 A1 | 2/2018 | Kurohara et al. |
| 2018/0093444 A1 | 4/2018 | Begrow et al. |
| 2018/0140473 A1 | 5/2018 | Koshijima et al. |
| 2018/0147095 A1 | 5/2018 | Koshijima et al. |
| 2018/0168880 A1 | 6/2018 | Schneider et al. |
| 2018/0169964 A1 | 6/2018 | Schneider et al. |
| 2018/0170027 A1 | 6/2018 | Schneider et al. |
| 2018/0280209 A1 | 10/2018 | Manabe et al. |
| 2019/0000162 A1 | 1/2019 | Houde |
| 2019/0021916 A1 | 1/2019 | Ishikawa |
| 2019/0070041 A1 | 3/2019 | Schneider et al. |
| 2019/0209396 A1 | 7/2019 | Nakamura et al. |
| 2019/0224053 A1 | 7/2019 | Nakamura et al. |
| 2019/0231606 A1 | 8/2019 | Andrews et al. |
| 2019/0274895 A1 | 9/2019 | Chen et al. |
| 2019/0358093 A1 | 11/2019 | Kaufman et al. |
| 2019/0374398 A1 | 12/2019 | Coenen et al. |
| 2019/0374404 A1 | 12/2019 | Ninomiya et al. |
| 2020/0039152 A1 | 2/2020 | Ehlert et al. |
| 2020/0179180 A1 | 6/2020 | Koshijima et al. |
| 2020/0197230 A1 | 6/2020 | Ohtsubo |
| 2020/0206040 A1 | 7/2020 | Andrews et al. |
| 2020/0206043 A1 | 7/2020 | Coenen et al. |
| 2020/0214901 A1 | 7/2020 | Andrews et al. |
| 2020/0268567 A1 | 8/2020 | Coenen et al. |
| 2020/0297551 A1 | 9/2020 | Andrews et al. |
| 2020/0298545 A1 | 9/2020 | Andrews et al. |
| 2020/0299883 A1 | 9/2020 | Begrow et al. |
| 2020/0360191 A1 | 11/2020 | Nakamura et al. |
| 2020/0361158 A1 | 11/2020 | Sugiura et al. |
| 2021/0000657 A1 | 1/2021 | Hohm et al. |
| 2021/0059866 A1 | 3/2021 | Fritz et al. |
| 2021/0100695 A1 | 4/2021 | Ishibashi et al. |
| 2021/0205152 A1 | 7/2021 | Polidori et al. |
| 2021/0252796 A1 | 8/2021 | Ehlert et al. |
| 2021/0267818 A1 | 9/2021 | Kaufman et al. |
| 2022/0000676 A1 | 1/2022 | Schneider et al. |
| 2022/0071809 A1 | 3/2022 | Fritz |
| 2022/0151840 A1 | 5/2022 | Mueller et al. |
| 2022/0211553 A1 | 7/2022 | Manabe |
| 2022/0218534 A1 | 7/2022 | Minami et al. |
| 2022/0250331 A1 | 8/2022 | Weiler et al. |

FOREIGN PATENT DOCUMENTS

| | | |
|---|---|---|
| EP | 0168225 B1 | 3/1991 |
| EP | 0330716 A3 | 7/1991 |
| EP | 0307871 B1 | 12/1992 |
| EP | 0386324 B1 | 6/1993 |
| EP | 685586 A2 | 12/1995 |
| EP | 886480 B1 | 12/2001 |
| EP | 1166721 A3 | 12/2003 |
| EP | 1035808 B1 | 3/2004 |
| EP | 1024721 B1 | 9/2004 |
| EP | 1351815 B9 | 6/2005 |
| EP | 677284 B2 | 8/2005 |
| EP | 1388410 B1 | 10/2005 |
| EP | 1448824 B1 | 10/2005 |
| EP | 1029521 B1 | 4/2006 |
| EP | 1138471 B1 | 6/2006 |
| EP | 1159942 B1 | 7/2006 |
| EP | 1641417 B1 | 6/2007 |
| EP | 1236827 B1 | 1/2008 |
| EP | 1547558 B1 | 10/2008 |
| EP | 1555000 A3 | 11/2008 |
| EP | 1290289 B1 | 12/2008 |
| EP | 1330355 B1 | 3/2009 |
| EP | 1263989 B1 | 5/2009 |
| EP | 1458553 B1 | 9/2009 |
| EP | 1330322 B8 | 10/2009 |
| EP | 1610950 B1 | 10/2009 |
| EP | 1715994 B1 | 3/2010 |
| EP | 1520569 B1 | 7/2010 |
| EP | 1586252 B1 | 8/2010 |
| EP | 1959907 B1 | 9/2010 |
| EP | 1525345 B1 | 4/2011 |
| EP | 1882177 B1 | 6/2011 |
| EP | 1707168 B1 | 8/2011 |
| EP | 1716831 B1 | 9/2011 |
| EP | 2083100 B1 | 9/2011 |
| EP | 2207926 B1 | 9/2011 |
| EP | 2219534 B1 | 9/2011 |
| EP | 2027841 B1 | 7/2012 |
| EP | 1595017 B1 | 8/2012 |
| EP | 1891256 B1 | 8/2012 |
| EP | 2020972 B1 | 11/2012 |
| EP | 2020974 B1 | 12/2012 |
| EP | 1685816 B1 | 1/2013 |
| EP | 2024178 B1 | 1/2013 |
| EP | 2088980 B1 | 1/2013 |
| EP | 2103427 A3 | 3/2013 |
| EP | 1272347 B1 | 4/2013 |
| EP | 1458565 B1 | 3/2014 |
| EP | 1575470 B1 | 6/2014 |
| EP | 2088981 B1 | 6/2014 |
| EP | 2431013 B1 | 9/2014 |
| EP | 2441866 B1 | 2/2015 |
| EP | 2727521 A4 | 3/2015 |
| EP | 1806117 B1 | 6/2016 |
| EP | 3028687 B1 | 3/2017 |
| EP | 1666178 B1 | 5/2017 |
| EP | 2214614 B1 | 8/2017 |
| EP | 3092997 B1 | 8/2017 |
| EP | 2450015 B1 | 11/2017 |
| EP | 2105115 B1 | 3/2018 |
| EP | 2116367 B1 | 4/2018 |
| EP | 2142261 B1 | 5/2018 |

(56) References Cited

FOREIGN PATENT DOCUMENTS

| | | | |
|---|---|---|---|
| EP | 2454957 | B1 | 11/2018 |
| EP | 3277480 | A4 | 3/2019 |
| EP | 3117810 | B1 | 7/2019 |
| EP | 3199132 | B1 | 9/2019 |
| EP | 3056176 | B1 | 10/2019 |
| EP | 3296100 | B1 | 1/2020 |
| EP | 3527181 | A4 | 6/2020 |
| EP | 3675784 | A1 | 7/2020 |
| EP | 3677231 | B1 | 7/2020 |
| EP | 3558192 | B1 | 1/2021 |
| EP | 3589251 | A4 | 1/2021 |
| EP | 3589252 | A4 | 1/2021 |
| EP | 3646830 | A4 | 3/2021 |
| EP | 3558664 | B1 | 4/2021 |
| EP | 3519162 | B1 | 7/2021 |
| EP | 3572052 | B1 | 7/2021 |
| EP | 3558193 | B1 | 8/2021 |
| EP | 3727254 | A4 | 8/2021 |
| EP | 3865103 | A1 | 8/2021 |
| EP | 3558191 | B1 | 9/2021 |
| EP | 3275413 | B1 | 10/2021 |
| EP | 3342385 | B1 | 10/2021 |
| EP | 3527182 | B1 | 10/2021 |
| EP | 3675785 | B1 | 11/2021 |
| EP | 3904057 | A1 | 11/2021 |
| EP | 3747636 | A4 | 12/2021 |
| EP | 3941738 | A1 | 1/2022 |
| EP | 3299167 | B1 | 3/2022 |
| EP | 3981371 | A1 | 4/2022 |
| EP | 3960439 | A4 | 6/2022 |
| EP | 3960140 | A4 | 7/2022 |
| EP | 4025412 | A1 | 7/2022 |
| FR | 2532337 | A1 | 3/1984 |
| JP | 2005095574 | A | 4/2005 |
| JP | 2008154998 | A | 7/2008 |
| JP | 2009056156 | A | 3/2009 |
| JP | 2009106667 | A | 5/2009 |
| JP | 5085239 | B2 | 11/2012 |
| JP | 05106990 | B2 | 12/2012 |
| JP | 05124188 | B2 | 1/2013 |
| JP | 2014198179 | A | 10/2014 |
| JP | 2017064130 | A | 4/2017 |
| JP | 06192003 | B2 | 9/2017 |
| JP | WO2018118573 | A1 | 6/2018 |
| KR | 1982464 | B1 | 5/2019 |
| KR | 20136008 | B1 | 8/2019 |
| KR | 2022211 | B1 | 9/2019 |
| RU | 2304047 | C2 | 8/2007 |
| RU | 2010125133 | A | 12/2011 |
| WO | WO1993021788 | A1 | 11/1993 |
| WO | WO0192013 | | 12/2001 |
| WO | WO2009067055 | A1 | 5/2009 |
| WO | WO2011087502 | A1 | 7/2011 |
| WO | WO2014109924 | B1 | 7/2014 |
| WO | WO2016033226 | A1 | 3/2016 |
| WO | WO2016109514 | A1 | 7/2016 |
| WO | WO2016160752 | A1 | 10/2016 |
| WO | WO2016208513 | A1 | 4/2018 |
| WO | WO2018097771 | A1 | 5/2018 |
| WO | WO2019070248 | A1 | 4/2019 |
| WO | WO2019125415 | A1 | 6/2019 |

OTHER PUBLICATIONS

Machine Translation for JP0516990 (B2).
Machine Translation for JP05124188 (B2).
Machine Translation for JP06192003 (B2).
Machine Translation for JP2008154998 (A).
Machine Translation for JP2009106667 (A).
Machine Translation for CN101868210 (B).
Machine Translation for EP0307871 (B1).
Machine Translation for EP0330716 (A3).
Machine Translation for EP0386324 (B1).
Machine Translation for EP1029521 (B1).
Machine Translation for EP1586252 (B1).
Machine Translation for EP2027841 (B1).
Presentation by Thomas Elhert, VP of RD&E, Aurizon Ultrasonics, LLC, entitled "Adhesive-free, Ultrasonic Elastic Attachment", date at least as early as Nov. 17, 2014, 57 pages.
Machine Translation for EP2207926 (B1).
Machine Translation for EP2431013 (B1).
Machine Translation for RU2010125133 (A).
Machine Translation for CN2304047 (C2).
PCT International Search Report and Written Opinion(1800.182_PCT), dated Jun. 4, 2021.
Japanese Office Action for Application No. JP2020-541440 dated Feb. 7, 2023.

\* cited by examiner

CURVED ELASTIC WITH ENTRAPMENT

CROSS-REFERENCE TO RELATED APPLICATIONS

The present application is a continuation of, and claims priority to, U.S. patent application Ser. No. 16/947,779, filed Aug. 17, 2020, which claims the benefit of U.S. Patent Application Ser. No. 62/896,063, filed Sep. 5, 2019, the disclosures of which are incorporated herein by reference in their entirety.

BACKGROUND OF THE INVENTION

Absorbent sanitary products, such as disposable diapers, are typically equipped with elastic composite structures that include one or more elastic threads. These elastic composite structures are positioned at various locations throughout the product, including in the waistbands, leg cuff regions, and throughout all or portions of the front or back panels of the product. During the typical manufacturing process of an elastic composite structure, the elastic threads are held in a tensioned state and an adhesive is used to secure the elastic threads between the two facing layers of non-woven materials or webs. The tension in the elastic threads is subsequently released, causing the web material to pucker or fold in the areas that contain the adhered elastic threads.

The use of adhesives to bond the elastic threads within elastic composite structures presents a number of disadvantages in both the end product and manufacturing method, including costs associated with the consumable material and undesirable tactile properties of the end product (e.g., stiffness). While thermal or ultrasonic welding techniques have been proposed as alternatives for bonding elastic threads within an elastic composite structure, movement or shifting of the elastic threads between or outside of notches on the anvil during the manufacturing process may result in a given elastic thread breaking or being unanchored over one or more portions of its length.

Accordingly, there is a need for an improved apparatus and method for fabricating an elastic composite structure of an absorbent sanitary product that reduces thread breakage and improves the reliability of bonds that anchor elastic threads in position within an elastic composite structure.

BRIEF STATEMENT OF THE INVENTION

Embodiments of the invention relate generally to absorbent sanitary products and, more particularly, to an improved apparatus and method for manufacturing an elastic composite structure including curved elastic entrapment for use in an absorbent sanitary product.

In accordance with one aspect of the invention, an apparatus for manufacturing an elastic composite structure includes a first roller configured to transport a web layer in a machine direction and a laydown guide configured to guide a laydown pattern of a plurality of elastic threads. A rotary anvil comprises a first weld line having a first notch formed in a contact surface of the first weld line, the first notch having a first interior configured to receive a portion of a first elastic thread of the plurality of elastic threads and a portion of the web layer therein. The first notch comprises a facing surface defining at least a portion of the first interior. A smallest orientation angle of a first face axis normal to the facing surface with respect to a contact surface axis normal to the contact surface is a first angle that is less than 90 degrees.

In accordance with another aspect of the invention, a bonding apparatus assembly for manufacturing an elastic composite structure comprises a first rotary anvil comprising a first weld line and comprises a second rotary anvil comprising a second weld line. The first weld line includes a first notch formed in a first contact surface of the first weld line, the first notch having a first interior configured to receive a first elastic thread and a first portion of a web layer therein. The first notch comprises a first facing surface defining a portion of the first interior, and a smallest orientation angle of a first face axis normal to the first facing surface with respect to a first contact surface axis normal to a plane of the first contact surface is a first angle that is less than 90 degrees. The second weld line comprises a second notch formed in a second contact surface of the second weld line, the second notch having a second interior configured to receive a second elastic thread and a second portion of the web layer therein. The second notch comprises a second facing surface defining a portion of the second interior, and an orientation angle of a second face axis normal to the second facing surface with respect to a second contact surface axis normal to a plane of the second contact surface is distinct from the smallest orientation angle of the first face axis.

In accordance with another aspect of the invention, a method for manufacturing an elastic composite structure comprises guiding, in a machine direction, a first web layer adjacently to a rotary anvil via a first roller and guiding an elastic thread adjacently to the rotary anvil via a laydown guide. The rotary anvil comprises a weld line having a notch formed in a contact surface of the weld line, the notch having an interior configured to receive a portion of the elastic thread and a portion of the first web layer therein. The notch comprises a facing surface defining at least a portion of the interior, and a smallest orientation angle of a first face axis normal to the facing surface with respect to a contact surface axis normal to the contact surface is a first angle that is less than 90 degrees.

BRIEF DESCRIPTION OF THE DRAWINGS

The drawings illustrate embodiments presently contemplated for carrying out the invention.

In the drawings.

DETAILED DESCRIPTION

Embodiments of the present invention provide for a method and apparatus for manufacturing an elastic composite structure usable in an absorbent sanitary product such as, for example, a diaper, disposable adult pant, or feminine care product.

During the manufacture of absorbent sanitary products, it is often desirable to secure elastic threads between facing layers of non-woven material to form contoured or elasticized regions within the product. Such products are typically manufactured on an assembly or manufacturing line in which the product moves substantially continually longitudinally in what is referred to as the "machine direction."

Figure 1:
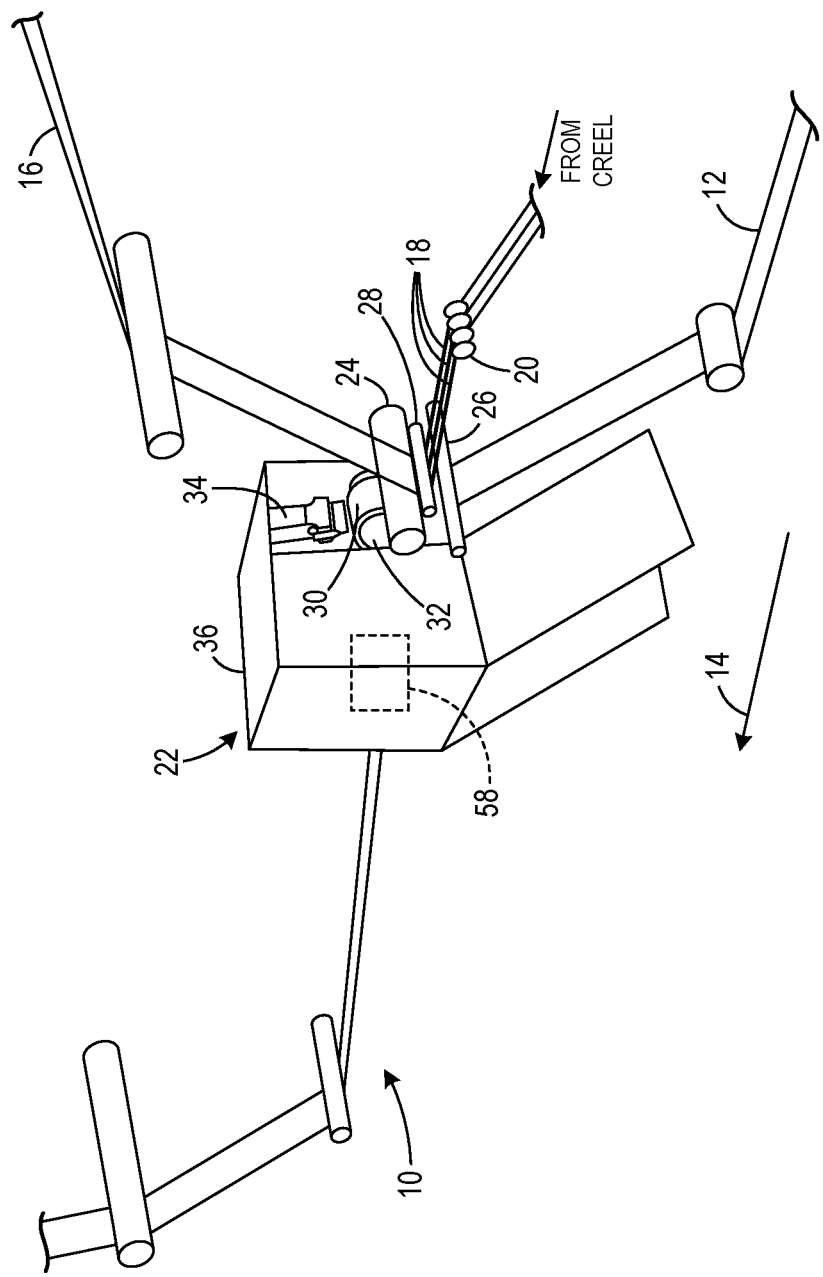
FIG. 1 is a schematic perspective view of a portion of a manufacturing line for fabricating an elastic composite structure.

Referring now to FIG. 1, a portion of an exemplary manufacturing line 10 is illustrated according to one embodiment of the invention. As shown, a first web layer 12 is fed in the machine direction 14. A second web layer 16 is similarly fed in the machine direction 14. First web layer 12 and second web layer 16 are materials capable of fusing to one another upon application of an applied energy that causes one or both of the webs 12, 16 to soften or melt and join together without the use of an intermediate layer of adhesive material such as glue. The facing pair of web layers 12, 16 may be the same type of material or different materials according to alternative embodiments. As non-limiting examples, first and second web layers 12, 16 may include nonwoven materials, woven materials, films, foams, and/or composites or laminates of any of these material types.

One or more elastic threads 18 are positioned between the first and second web layers 12, 16. While the below description refers to elastic threads in the plural form, it is to be understood that the methods described herein may be used to manufacture an elastic composite structure that includes a single elastic thread or any number of multiple elastic threads. The elastic threads 18 travel in the machine direction 14 under tension from a creel assembly (not shown) or similar device. The elastic threads 18 may be composed of any suitable elastic material including, for example, sheets, strands or ribbons of thermoplastic elastomers, natural or synthetic rubber, or elastic strands such as LYCRA, as non-limiting examples. Each elastic thread 18 may be provided in the form of an individual elastomeric strand or be a manufactured multifilament product that includes many individual elastomeric filaments joined together, such as by a dry-spinning manufacturing process, to form a single, coalesced elastic thread 18.

Elastic threads 18 may have any suitable cross-sectional shape that facilitates formation of an elastic composite structure having desired elasticity, visual aesthetic, and manufacturability. As non-limiting examples, elastic threads 18 may have a cross-sectional shape that is round, rectangular, square, or irregular as may be the case where each elastic thread 18 is a multifilament product.

While first web layer 12 and second web layer 16 are depicted in FIG. 1 and described herein as physically separate components, it is contemplated that alternative embodiments may utilize a unitary web structure that is folded to capture the elastic threads 18 between upper and lower layers of the unitary web structure. In such an embodiment, the portion of the unitary structure positioned below the elastic threads 18 would be referred to as the first web layer 12 and the portion of the unitary structure positioned above the elastic threads 18 would be referred to as the second web layer 16.

Manufacturing line 10 includes one or more feeding assemblies 20 such as guide rollers that are employed to accurately position and (optionally) tension the elastic threads 18 as they travel in the machine direction 14 toward a bonding apparatus 22. Immediately upstream of the bonding apparatus 22 are one or more assemblies that feed and guide the first and second web layers 12, 16 and the elastic threads 18 into the bonding apparatus 22. In the illustrated embodiment, these feeding assemblies 20 include an upper roller 24, a lower roller 26, and a strand guide roller 28 that guide a combined assembly 30 that includes the first web layer 12, the second web layer 16, and the elastic threads 18 into the bonding apparatus 22. It is contemplated that rollers 24, 26, 28 may be replaced with other known types of feeding assemblies and/or replaced by a single roller unit or other known type of feeding assembly in an alternative embodiment.

Bonding apparatus 22 may be any known ultrasonic welding system in alternative embodiments, including, as non-limiting examples, a rotary ultrasonic welding system or a blade ultrasonic welding system. In the illustrated embodiment, bonding apparatus 22 includes a rotary anvil 32 and an ultrasonic fixed blade horn 34, also known as a sonotrode, which cooperate with each other to bond (i.e., fuse) the first web layer 12 to the second web layer 16. Alternative embodiments may include multiple fixed blade horns or one or more rotary horns. During the bonding process the elastic threads 18 are secured or anchored in position relative to the first and second web layers 12, 16 as described in detail below.

Bonding apparatus 22 also includes one or more frames 36 that support and/or house a motor (not shown) that drives the ultrasonic horn 34, a vibration control unit (not shown) that ultrasonically energizes the horn 34 and causes the horn 34 to vibrate, and a second motor (not shown) that drives the anvil 32. The horn 34 and anvil 32 are positioned in a spaced relationship relative to one another to facilitate ultrasonically bonding the first and second web layers 12, 16 to one another while the elastic threads 18 are held in tension in the space between the horn 34 and anvil 32. During the bonding process, the first and second web layers 12, 16 are exposed to an ultrasonic emission from the horn 34 that increases the vibration of the particles in the first and second web layers 12, 16. The ultrasonic emission or energy is concentrated at specific bond points where frictional heat fuses the first and second web layers 12, 16 together without the need for consumable adhesives. While bonding apparatus 22 is described herein as an ultrasonic bonding assembly that ultrasonically fuses first web layer 12 to second web layer 16, it is contemplated that the techniques described herein may be extended to any other known welding or bonding techniques that fuse together two or more material layers without the use of adhesive, including sonic, thermal, or pressure bonding techniques and various other forms of welding known in the industry.

Figure 2:
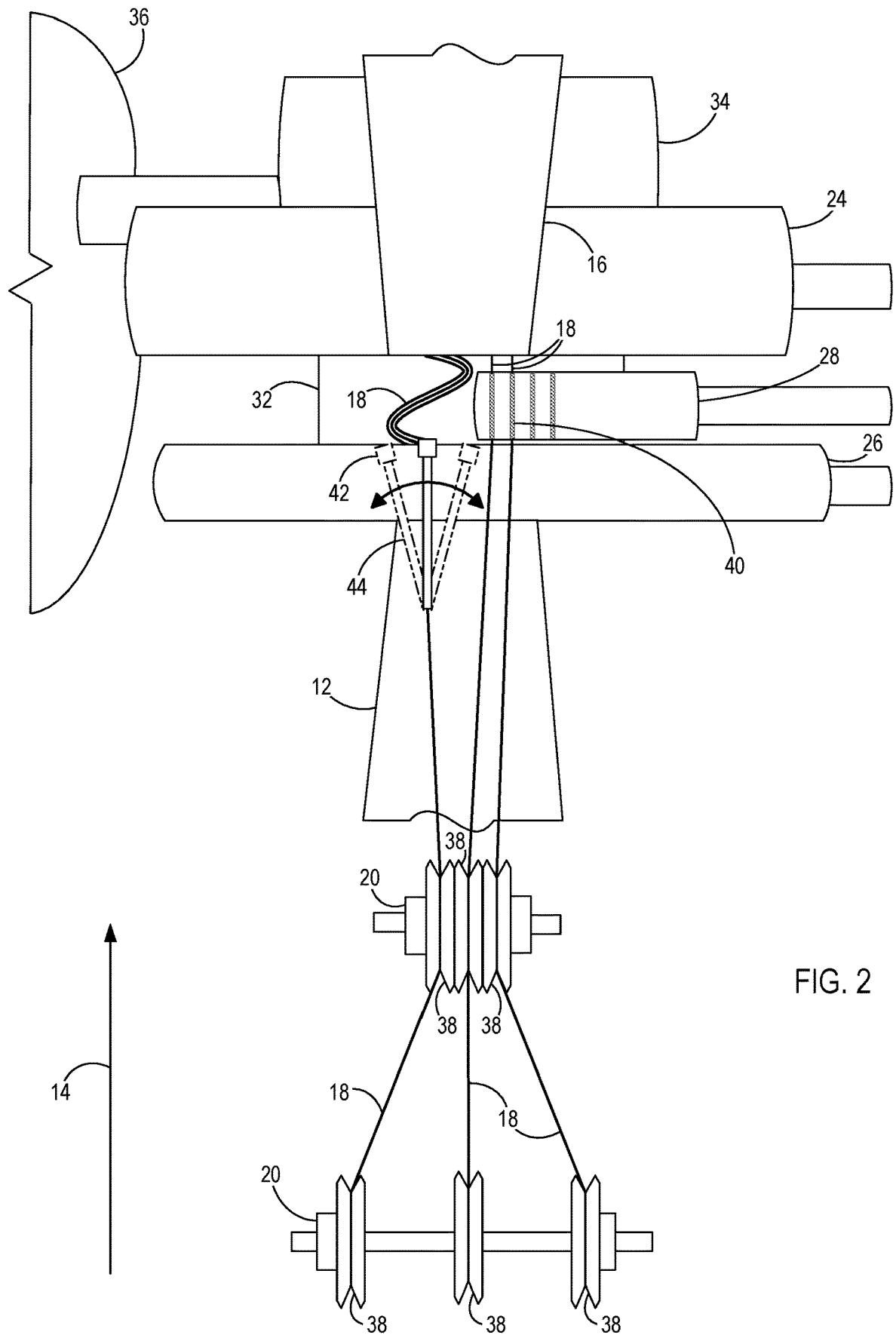
FIG. 2 is a schematic perspective view of a portion of the manufacturing line of FIG. 1 according to one embodiment of the invention.

FIG. 2 is a view of a portion of the manufacturing line 10 upstream of the ultrasonic bonding apparatus 22 looking into the machine direction 14. As shown, elastic threads 18 are positioned within a respective guiding section 38 of feeding assembly 20 to maintain separation between the elastic threads 18. Each guiding section 38 may be used to guide a single elastic thread 18 as shown, or multiple threads 18 in alternative embodiments. In the illustrated embodiment, guiding section 38 includes notches 40 that aid in alignment and guiding of the elastic threads 18. Notches may be v-shaped as shown, have curved or other alternative geometries, or be omitted entirely in alternative embodiments.

A portion of the elastic threads 18 is fed outward from respective guiding sections 38 in the feeding assembly 20 and toward strand guide roller 28. In the illustrated embodiment, strand guide roller 28 includes an array of notches 40 that aid in aligning and guiding the elastic threads as they are received between the horn 34 and anvil 32. These notches 40 may be evenly spaced across all of the strand guide roller 28 in the manner shown or may span only a portion thereof in an alternative embodiment. In yet other embodiments, the notches 40 may be positioned at uneven intervals along the length of strand guide roller 28 depending upon design specifications and the desired placement and spacing of the elastic threads 18 in the resulting elastic composite structure. Placement of the elastic threads 18 by the notches 40 allows for linear positioning of the elastic threads 18 along the anvil 32 for elastic sections such as waist or belly elastic portions.

Also shown in FIG. 2 is an elastic laydown guide 42 provided with the ability to make side-to-side excursions by an arm 44 that generally travels side to side (e.g., by a swinging motion) or slides side to side. The side-to-side excursions of the elastic laydown guide 42 may result a laydown pattern generally including arcuate segments of elastic strands along the anvil 32 for nonlinear elastic sections such as leg or leg cuff elastic portions or other curved waist elastic portions. Each elastic laydown guide 42 may guide one or more elastic threads 18 simultaneously. The elastic laydown guide 42 may also operate to lay down a linear pattern for linear elastic sections.

Figure 3:
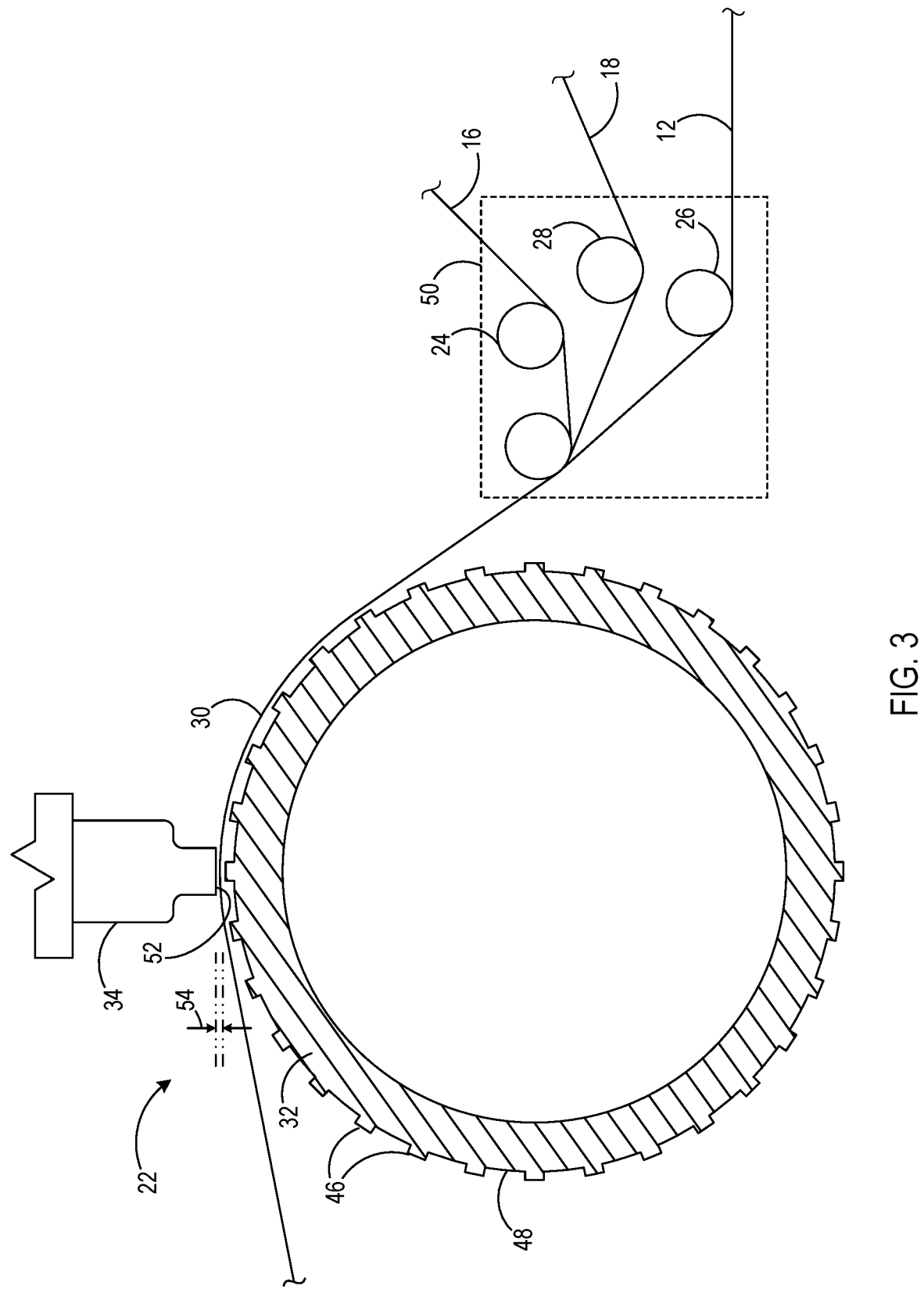
FIG. 3 is a schematic cross-sectional view of a bonding apparatus that is usable with the manufacturing line of FIG. 1 according to one embodiment of the invention.

Referring to FIG. 3, anvil 32 is illustrated according to one embodiment of the invention. As shown, the anvil 32 of includes an arrangement of discrete projections or welds 46 that extend outward from the anvil face 48. These welds 46 are constructed to (A) fuse first and second web layers 12, 16 together and (B) restrain or anchor the elastic threads 18 in position relative to the first and second web layers 12, 16 in the manufactured elastic composite structure. As described in more detail below, anchoring projections 46 are designed so that an elastic thread 18 that passes between two adjacent anchoring projections 46 on the face 48 of anvil 32 is anchored in position relative to the first and second web layers 12, 16 by frictional resistance that prevents the elastic thread 18 from sliding through the pair of resulting bonds.

As illustrated in FIG. 3, a roller assembly 50 includes guide rollers 24, 26, 28 that are employed to accurately position and (optionally) tension the elastic threads 18 and the first and second web layers 12, 16 as they travel toward the bonding apparatus 22. It is contemplated that rollers 24, 26, 28 may be replaced with other known types of feeding assemblies and/or replaced by a single roller unit or other known type of feeding assembly in an alternative embodiment.

The particular size, shape, and general arrangement of anchoring projections 46 as well as the total number of projections 46 illustrated in FIG. 3 are intended to depict a representative and non-limiting example of an overall pattern of projections 46 on anvil 32. Alternative embodiments may include any number of projections 46 arranged in any number of alternative configurations to achieve a desired pattern of bonds on the end product. The respective working surfaces of anchoring projections 46 may be configured to form bonds of similar size and shape, or bonds of different size and/or shape in alternative embodiments. As non-limiting examples, respective land surfaces of anchoring projections 46 may be circular, rectangular, crescent shaped, or have irregular shapes that may be selected to form a desired overall pattern on the end product. The resulting pattern of bonds will include one or more anchored zones, which fix one or more elastic threads 18 under tension in position relative to the first and second web layers 12, 16.

In a preferred embodiment the anchoring projections 46 are formed on anvil 32 using a machining process that removes bulk material from the anvil 32 to create the desired raised pattern of projections 46 relative to the face 48 of the anvil 32. Alternatively, anchoring projections 46 may be provided on one or more inserts that are mechanically coupled to the face 48 of the anvil 32.

Still referring to FIG. 3, the working surface 52 of the horn 34 has a smooth or substantially smooth surface contour in one non-limiting embodiment. Alternatively, working surface 52 may include an arrangement of projections 46 that mate or align with the pattern of projections 46 on the anvil 32 to further facilitate fusing the first web layer 12 to the second web layer 16 and securing the elastic threads 18 in position relative to the first and second web layers 12, 16.

Figure 4:
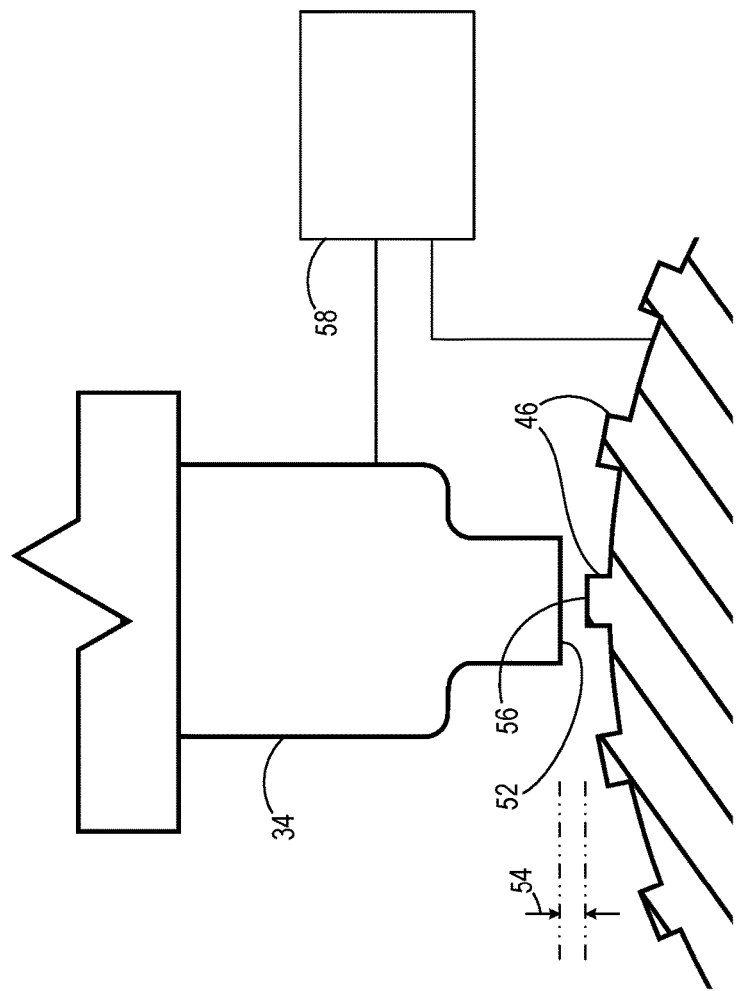
FIG. 4 is a detailed view of a portion of the bonding apparatus of FIG. 3 illustrating the horn aligned with an anchoring weld on the rotary anvil, according to one embodiment of the invention.

During the manufacturing process, the first and second web layers 12, 16 are positioned between the face 48 of the anvil 32 and the working surface 52 of the horn 34 as shown in FIG. 3. Elastic threads 18 are positioned between the first and second web layers 12, 16 in a tensioned state. As generally shown in FIG. 3 and in further detail in FIG. 4, the position of horn 34 is controlled to maintain a nip gap 54 between the working surface 52 of horn 34 and the land surfaces 56 of the anchoring projections 46. The size of the nip gap 54 is determined based on parameters of the manufacturing process to facilitate bonding between the first and second web layers 12, 16. Bonding apparatus 22 may include any known positioning means 58 that exerts a force on at least one of the horn 34 and anvil 32 to maintain a desired nip gap 54 between the horn 34 and anvil 32. Positioning means 58 may be an air pressure assembly (not shown) or a mechanical camshaft (not shown) as non-limiting examples.

Anchoring projections 46 may have a planar working surface, planar side surfaces, or some mixture of curved and straight working and side surfaces in alternative embodiments. In the embodiment illustrated in FIG. 4, the land surface 56 of anchoring projection 46 has planar working and side surfaces. In alternative embodiments where the land surface 56 has an arced or curved surface profile, this curved profile permits the first and second web layers 12, 16 to slip relative to the face 48 of the anvil 32 during the bonding process and thus allows the velocity at which the combined assembly 30 including tensioned elastic strands 18 and first and second web layers 12, 16 is advanced toward the bonding apparatus 22 to be increased or decreased relative to the rotational velocity of the anvil 32. When the combined web/thread assembly 30 is advanced at a velocity greater than the velocity of the anvil 32, the resulting bonds are spaced apart by a distance greater than the radial spacing between of adjacent projections 46 on the anvil face 48. Similarly, slowing the feed rate of the combined web/thread assembly 30 relative to the velocity of the anvil 32 will result in bonds that are spaced apart by a distance less than the radial spacing between of adjacent projections 46 on the anvil face 48. The velocity mismatch or differential between web speed and anvil velocity can be controlled to accommodate size changes in the end product. As a result, the bonding of an elastic composite for one size diaper may be carried out with little or no slip, while the bonding of an elastic composite for a larger or smaller diaper may be carried out with a larger amount of slip. A manufacturing line 10 outfitted with an anvil that includes projections 46 with curved surface profiles thus provides for dynamic size changing without having to change the tooling set-up of the manufacturing line, as the same anvil can be used to manufacture multiple sizes of elastic composite structures for use in different sized products.

Figure 5A:
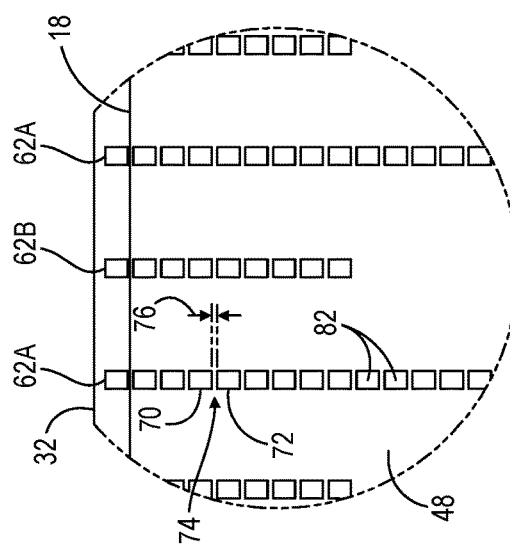
FIG. 5A is a detailed view of a portion of the rotary anvil of FIG. 5.
Figure 5:
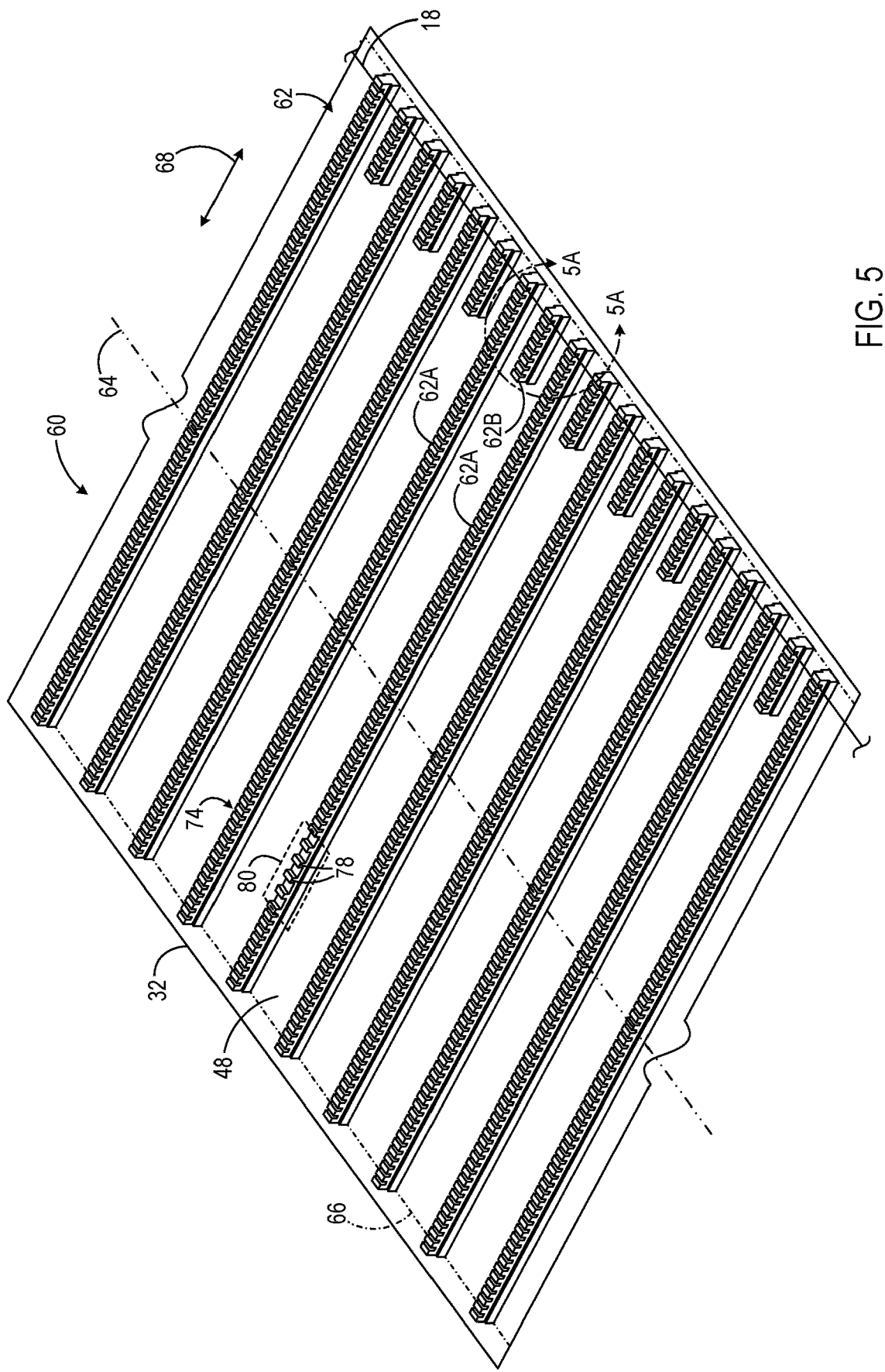
FIG. 5 is a flattened representation of an exemplary anvil pattern usable with the manufacturing line of FIG. 1 according to one embodiment of the invention.

FIG. 5 is a flattened representation of the circumferential face 48 of anvil 32 according to an embodiment where anvil 32 includes a pattern of projections 60 that form anchored zones. The pattern of projections 60 includes multiple anchoring weld lines 62 that are spaced apart from one another along the circumferential axis 64 of the anvil face 48. The anchoring weld lines 62 define an anchoring region 66 of the projection pattern 60. As with anchoring projections 46 above, in a preferred embodiment, the anchoring weld lines 62 are formed on anvil 32 using a machining process that removes bulk material from the anvil 32 to create the desired raised pattern of anchoring weld lines 62 relative to the face 48 of the anvil 32. Alternatively, anchoring weld lines 62 may be provided on one or more inserts that are mechanically coupled to the face 48 of the anvil 32.

FIG. 5 illustrates anchoring weld lines 62 that extend across substantially the entire longitudinal direction 68 of the rotary anvil 32 (e.g., lines 62A) as well as shorter anchoring weld lines 62 (e.g., lines 62B) that only partially extend along the longitudinal direction. The longitudinal direction 68 generally extends in the cross-machine direction. The bonds or joints formed by the section of the rotary anvil 32 absent the anchoring weld lines 62B are spaced farther apart than the bonds formed by the section including the anchoring weld lines 62B. The closer-spaced bond joints formed by the section including the anchoring weld lines 62B may be preferred when bonding the elastic threads 18 and first and second web layers 12, 16 (not shown in FIG. 5; see FIGS. 1, 2, 3, for example) together in a waist cap portion of the elastic web. However, the spacing between adjacent anchoring weld lines 62 as well as the length and placement of each anchoring weld line 62 along the longitudinal direction 68 may be subject to the design of the bond pattern desired in the finished product.

As shown more specifically in the detailed view provided in FIG. 5A, each weld line 62 contains a pattern of discrete projections 70, 72 that extend outward away from the face 48 of the anvil 32. The projections 70, 72 are spaced apart from one another, by a notch 74 that is defined by the width of a gap 76 positioned between a given pair of adjacent projections 70, 72. The width or size of the gap 76 may anchor one or more elastic threads 18 between adjacent bonds formed by projections 70, 72 such that the elastic thread(s) 18 is held tightly between the adjacent bonds. In this manner, for example, the adjacent bonds constrain the elastic thread(s) 18 such that the elastic thread(s) 18 is retained between the adjacent bonds in the case of a breakage of the elastic thread(s) 18.

Anvil 32 may in addition or alternatively include one or more projections that are referred to herein as laminating or non-anchoring projections 78. As illustrated in FIG. 5, a plurality of lamination projections 78 are shown in a lamination portion 80 of one of the anchoring weld lines 62A. Lamination projections 78, similar to the restraining or anchoring projections 70, 72, fuse first and second web layers 12, 16 to one another. Laminating projections 78 differ from anchoring projections 70, 72 because they do not anchor the elastic threads 18 in position relative to the first and second web layers 12, 16. Accordingly, a broken elastic thread 18 will contract out of the gap between the adjacent lamination weld bonds in contrast to that described above with respect to the anchoring weld bonds. Such laminating projections 78 are advantageous when laminating the first and second web layers 12, 16 in areas designed for elastic deactivation in which the elastic threads 18 are purposely broken in order to create a non-elastic portion of the bonded web layers 12, 16. While only a few of the lamination projections 78 are illustrated in FIG. 5, embodiments of the invention contemplate the use or non-use of any number and placement of the lamination projections 78.

Referring again to FIG. 5A, it is contemplated that the contact surfaces 82 of the projections 70, 72 may have different geometries in alternative embodiments. As non-limiting examples, projections 70, 72 may be circular, rectangular, crescent shaped, or have irregular shapes that may be selected to form a desired overall pattern on the end product. In yet another embodiment, corresponding projections 70, 72 of adjacent weld lines 62 may be aligned with one another in a line parallel to the circumferential axis 64 (FIG. 5). Alternatively, projections 70, 72 of sequential weld lines 62 may be offset from one another in the cross-machine direction thereby defining a stepped or non-linear passage through the bond lines that are formed on the first and second web layers 12, 16.

Figure 6:
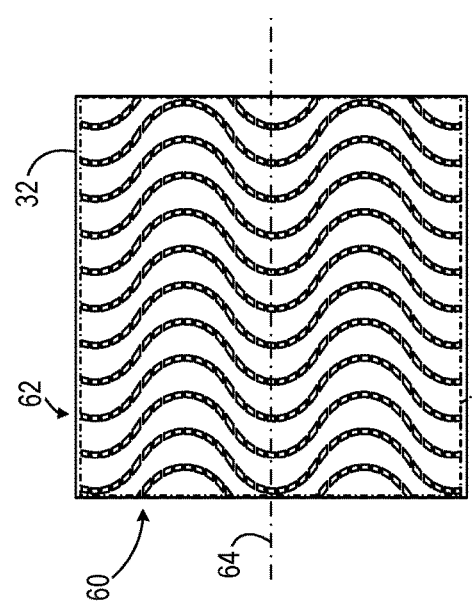
FIG. 6 is a flattened representation of an exemplary anvil pattern usable with the manufacturing line of FIG. 1 according to another embodiment of the invention.

FIG. 6 illustrates a non-linear arrangement of the anchoring weld lines 62 according to another embodiment of the invention. A sinusoidal pattern is shown that, when the elastic threads 18 (FIG. 1) and first and second web layers 12, 16 (FIG. 1) are bonded together, creates a distinctive gathering pattern as compared with the gathering pattern formed using the linear arrangement shown in FIG. 5. It is contemplated that other arrangement patterns may be formed into the anchoring weld lines 62 in other embodiments of the invention. Such other arrangement patterns may bond the elastic threads 18 and first and second web layers 12, 16 together in geometric or other patterns arranged in straight lines, curved lines, or otherwise arranged to create logos, pictures, other continuous and repeating patterns, or other designs on the end product.

Figure 7:
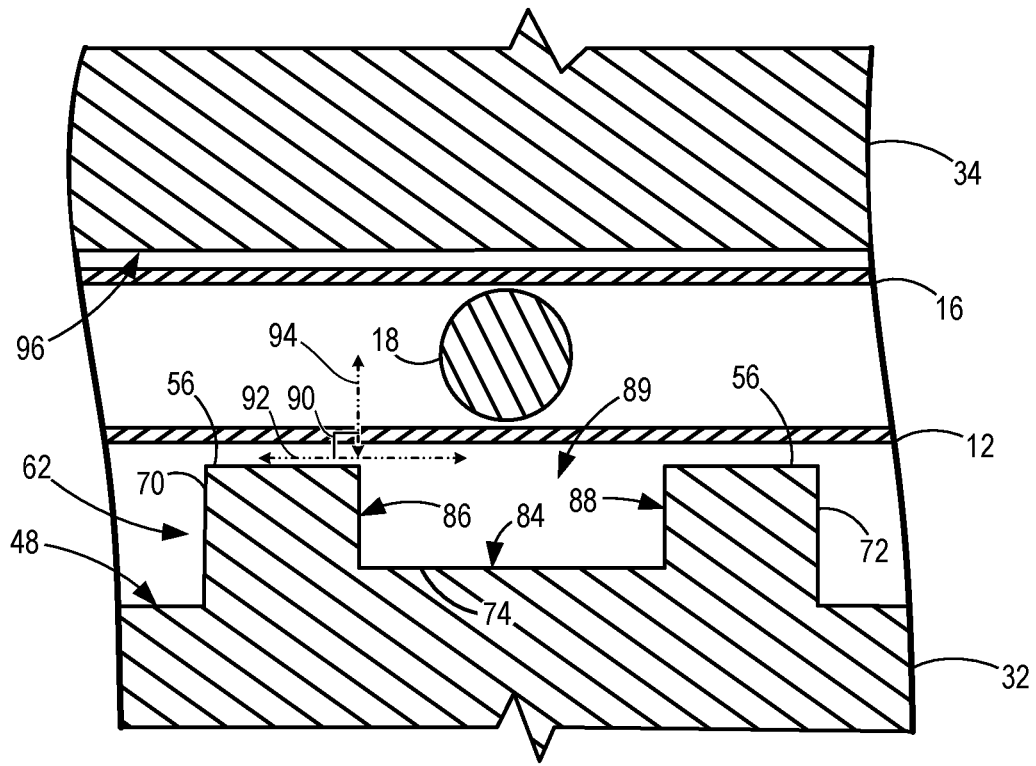
FIG. 7 is a cross-sectional view of a portion of a bonding unit usable with the manufacturing line of FIG. 1, according to one embodiment of the invention.

Referring now to FIG. 7, a cross-sectional view of a portion of the anvil 32 and horn 34 is provided according to one embodiment of the invention. As shown, the face 48 of the anvil 32 includes a weld line 62 that is defined by at least one notch 74, which is positioned between a corresponding pair of projections 70, 72. While only one instance of a notch 74 and corresponding pair of projections 70, 72 is illustrated in FIG. 7, it is contemplated that each weld line 62 on the anvil 32 may alternatively include multiple notches 74, with each notch 74 similarly arranged between a corresponding pair of projections 70, 72. In the embodiment shown, notch 74 has a u-shaped geometry defined by a bottom surface 84 and facing surfaces 86, 88 of the projections 70, 72. Surfaces 84, 86, 88 also define an interior 89 of the notch 74. Facing surfaces 86, 88 are oriented such that an angle 90 of an axis 92 (e.g., a face axis) normal to the surfaces 86, 88 is orthogonal with respect to an axis 94 (e.g., a contact surface axis) normal to the land surfaces 56 or contact surface 82. One or more of surfaces 84, 86, 88 may be planar, as shown, or curved in alternative embodiments.

Figure 8:
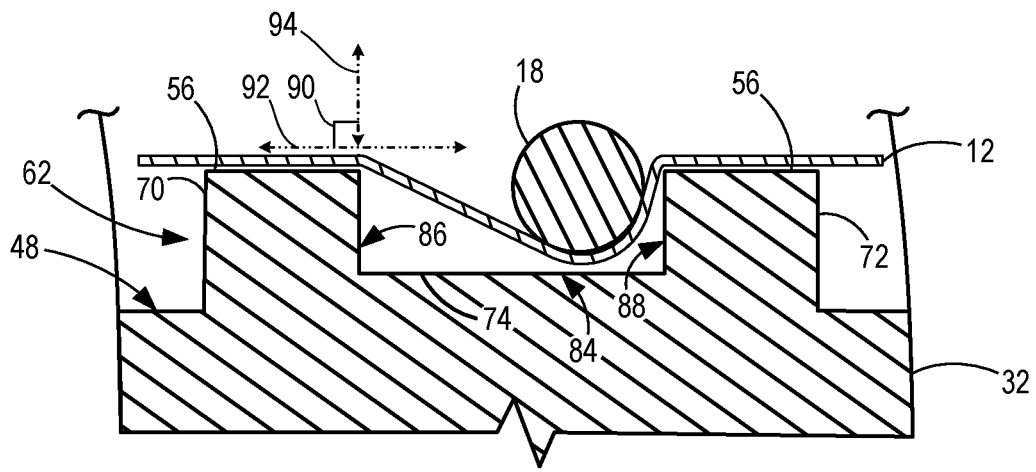
FIG. 8 is a cross-sectional view of a portion of the bonding unit of FIG. 7 during insertion of an elastic strand into a rotary anvil slot according to an embodiment.

During the manufacturing process, the first and second web layers 12, 16 are positioned between the face 48 of the anvil 32 and the face 96 of the horn 34. An elastic thread 18 is positioned between the first and second web layers 12, 16 in a tensioned state and aligned above notch 74. As shown in FIG. 8, as elastic thread 18 is inserted into notch 74, second web layer 16 is pulled into notch 74. The orientation of the surfaces 86, 88, when in an orthogonal orientation with respect to the land surfaces 56 as shown, allows the first web layer 12 to create slanted surfaces within the notch 74 that allow the elastic thread 18 to slip out of the notch 74, especially when creating curved elastic sections as shown in FIG. 2 where the tension on elastic thread 18 tends to pull the thread 18 toward the right of FIG. 8 as the elastic laydown guide 42 (FIG. 1) rotates to the right. A similar situation can occur when the elastic laydown guide 42 rotates to the left.

Figure 9:
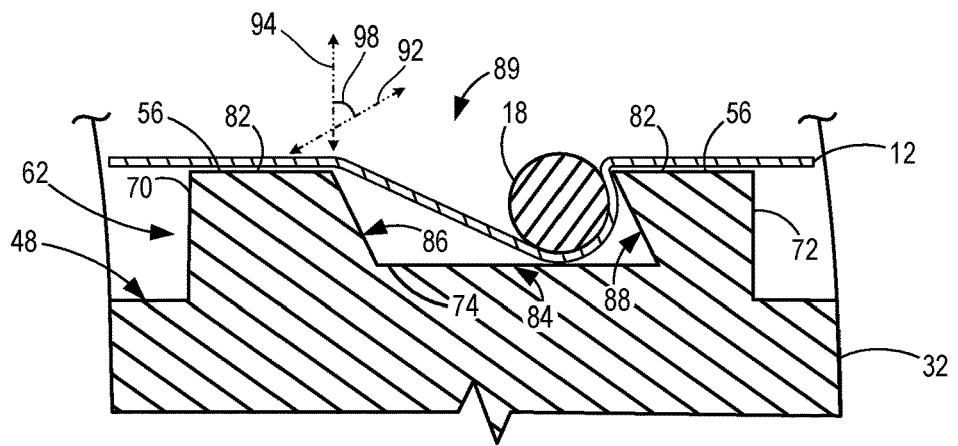
FIG. 9 is a cross-sectional view of a portion of the bonding unit of FIG. 7 during insertion of an elastic strand into a rotary anvil slot according to another embodiment.

Accordingly, an improved notch geometry is illustrated in FIG. 9. As illustrated, facing surfaces 86 and 88 are oriented in a non-vertical direction such that the elastic forces acting on the first web layer 12 and notch surfaces 84, 88 tend to keep the elastic strand 18 within the notch 74. As indicated by the smallest angle 98 between axis 92 and axis 94, the orientation of the facing surfaces 86, 88 is less than 90 degrees with respect to the contact surfaces 82 or land surfaces 56 of the projections 70, 72.

The side-to-side excursions of the elastic laydown guide 42 can pull the elastic thread 18 to one side of the notch 74 or the other. As illustrated in FIG. 9, the elastic thread 18 is seated toward the lower, right corner of the notch 74 that would be caused, for example, by the elastic laydown guide 42 being farther toward the right of the rotary anvil 32 than the position illustrated in FIG. 9 for the elastic thread 18 and by the tension of the elastic thread 18. In general, the farther the elastic laydown guide 42 is to one side or the other of the respective notch 74 and the stronger the elastic tension, the farther the elastic thread 18 will be pulled or forced into a respective corner of the notch 74. Embodiments of the invention, including the angled facing surface 88, minimizes slipping of the elastic thread 18 out of the notch 74.

Figure 10:
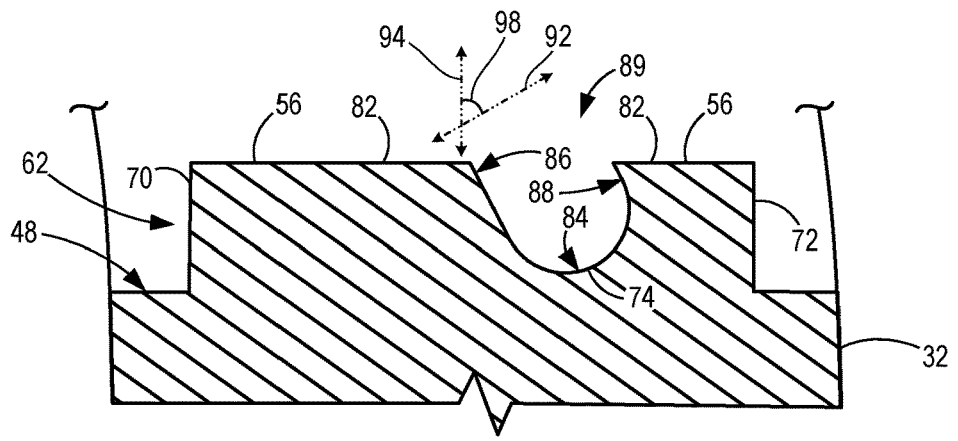
FIG. 10 is a cross-sectional view of a portion of the bonding unit of FIG. 7 during insertion of an elastic strand into a rotary anvil slot according to another embodiment.

FIG. 10 also illustrates that the orientation of the facing surfaces 86, 88 is less than 90 degrees with respect to the contact surfaces 82 or land surfaces 56 of the projections 70, 72. An alternate bottom surface 84 is also illustrated as being curved or rounded, which can be more fitting to the rounded elastic thread 18 than a flat surface.

Figure 11:
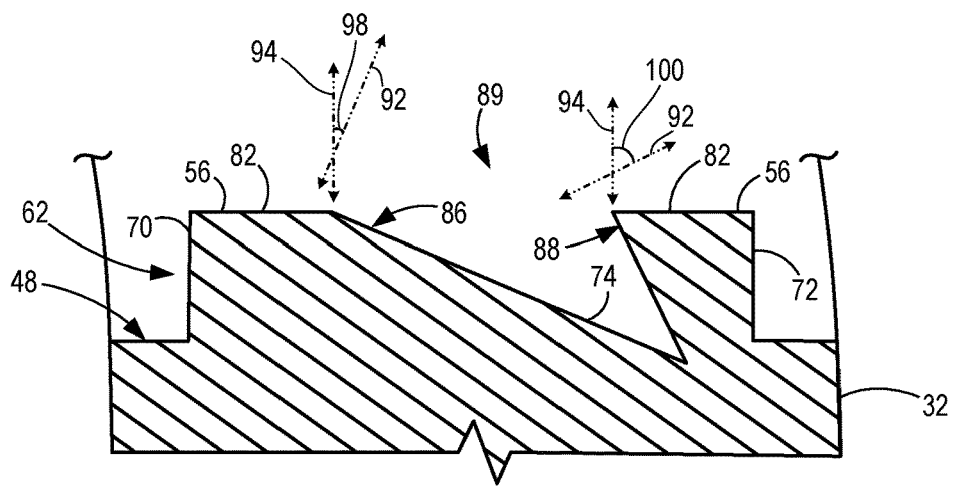
FIG. 11 is a cross-sectional view of a portion of the bonding unit of FIG. 7 during insertion of an elastic strand into a rotary anvil slot according to another embodiment.

As illustrated in FIGS. 9 and 10, the orientation of the axis 94 of the facing surfaces 86, 88 can be at the same smallest angle 98 with respect to axis 92 that is less than 90 degrees. However, as shown in FIG. 11, different orientation angles 98, 100 are contemplated where both angles 98, 100 are distinct but less than 90 degrees with respect to the contact surfaces 82 of the projections 70, 72. The bottom surface 84 can also be eliminated as illustrated in FIG. 11. For example, the facing surfaces 86, 88 may intersect one another at the maximum depth of the notch 74.

It is contemplated that the orientation of the facing surfaces 86, 88 of each notch 74 in the anchoring weld line 62 can vary and be independent of one another. Furthermore, the orientation of the facing surfaces 86, 88 of each notch 74 in adjacent anchoring weld lines 62 can be different along the circumference of the rotary anvil 32. For instance, in one section of the rotary anvil 32 where the elastic forces of the elastic threads 18 will tend to pull the threads 18 to the right due to their placement via the elastic laydown guide 42, the orientation of the facing surfaces 86, 88 of the notches 74 can be as illustrated in any of FIG. 9, 10, or 11 or in any combination thereof. In another section of the rotary anvil 32 where the elastic forces of the elastic threads 18 will tend to pull the threads 18 to the left due to their placement via the elastic laydown guide 42, the orientation of the facing surfaces 86, 88 of the notches 74 can be in a mirrored orientation with respect to that illustrated in FIG. 9, 10, or 11. The orientation of the notch facing surfaces 86, 88 can thus swing from a rightward elastic force orientation to a leftward elastic force orientation along the circumference of the rotary anvil 32 including an orientation in which the facing surfaces 86, 88 are vertically oriented. Accordingly, different sections of the rotary anvil 32 can be prepared to accept curved elastic portions or straight elastic portions as desired.

Figure 12:
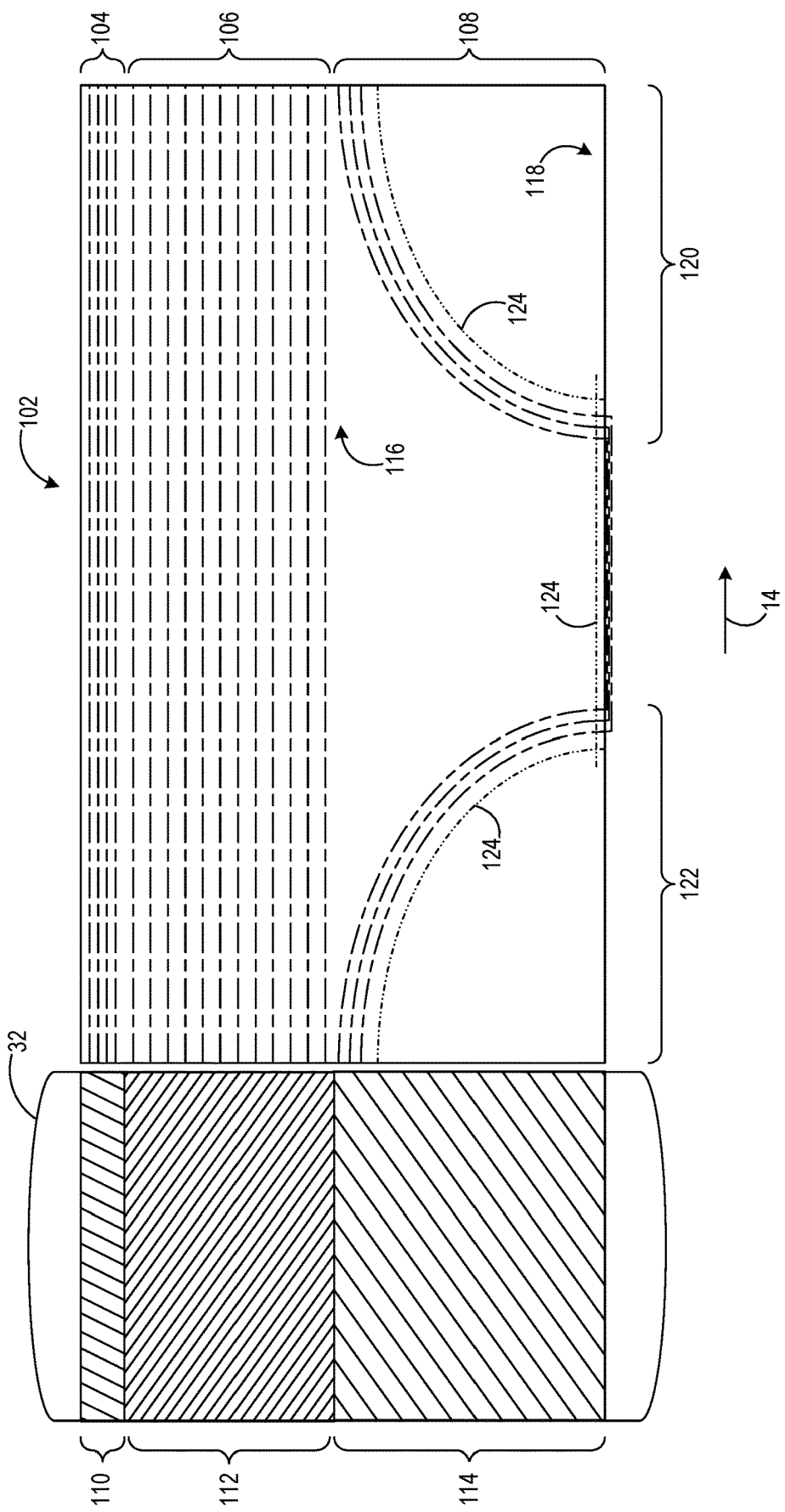
FIG. 12 is a schematic view of a multi-section rotary anvil according to an embodiment.

FIG. 12 illustrates a schematic view of the rotary anvil 32 having such different sections. An elastic web 102 usable in the formation of a front or back portion of a disposable product such as a diaper includes a waist cap elastic portion 104, a belly elastic portion 106, and a leg elastic portion 108. The waist cap elastic portion 104 can include a dense portion of elastic threads elastic thread 18 such that adjacent notches 74 of the anchoring weld lines 62 are used. For example, referring to FIG. 5, all eight notches 74 of anchoring weld lines 62B together with the corresponding notches 74 in the adjacent weld lines 62A may be used; however, it is contemplated that a fewer number of elastic threads 18 may be used. The belly elastic portion 106 can include a less-dense portion of elastic threads elastic thread 18 such that one or more empty notches 74 may exist between used notches 74 of the anchoring weld lines 62.

The waist cap elastic portion 104 and the belly elastic portion 106 may have a corresponding waist cap anvil portion 110 and belly anvil portion 112 on the rotary anvil 32, respectively. Since the elastic threads 18 laid down in the waist cap anvil portion 110 and the belly anvil portion 112 are substantially straight, it is not necessary to use a pivoting elastic laydown guide 42 in these areas but to use the notches 74 in the strand guide roller 28; however, a pivoting elastic laydown guide 42 may be used and held in a static position according to an embodiment. Furthermore, the notches 74 in the waist cap anvil portion 110 and the belly anvil portion 112 may be oriented in a vertical orientation as shown in FIG. 7 if no curves are expected to the elastic threads 18 in these regions.

A leg anvil portion 114 of the rotary anvil 32 corresponding to the leg elastic portion 108 may have the notches 74 of the anchoring weld lines 62 angled and varying as disclosed herein. For example, the notches 74 may be formed as shown in any of FIGS. 9-11 or the like. Furthermore, as indicated for the leg elastic portion 108 shown in FIG. 12, the elastic threads 18 are placed in this region in a curved manner extending from an inside edge 116 of the leg elastic portion 108 toward an outside edge 118 thereof. While traveling in the machine direction 14, the elastic threads 18 are moved from the inside edge 116 toward the outside edge 118 in a first leg portion 120 and from the outside edge 118 toward the inside edge 116 in a second leg portion 122. In a running web operation, second leg portion 122 immediately precedes the first leg portion 120 to create a continuous curved elastic region meant to border the leg opening to be formed therein.

The portion of the anchoring weld lines 62 corresponding with the first leg portion 120 may have their notches 74 angled oppositely to those corresponding with the second leg portion 122 to account for a change in the direction of the elastic force as the elastic threads 18 are positioned by the elastic laydown guide(s) 42. Furthermore, the angles of the notches 74 may change or vary within a leg portion 120, 122 to become more or less acute as needed. For example, as an elastic force becomes stronger as the rotary anvil 32 rotates, the angles/orientations of the corresponding notches 74 may become increasingly acute.

While FIG. 12 illustrates a single rotary anvil 32 having multiple sections (e.g., 110, 112, 114), embodiments of the invention include separate anvils having correspondingly-formed anchoring weld lines 62 that are positioned adjacently to one another. In a preferred embodiment, the separate anvils have a similar circumference, are positioned adjacently to one another, and are configured to rotate about a common rotation axis. The separate anvils may share a same axle, for example. However, the patterns and orientations of the anchoring weld lines 62 on each anvil may be distinct.

Figure 13:
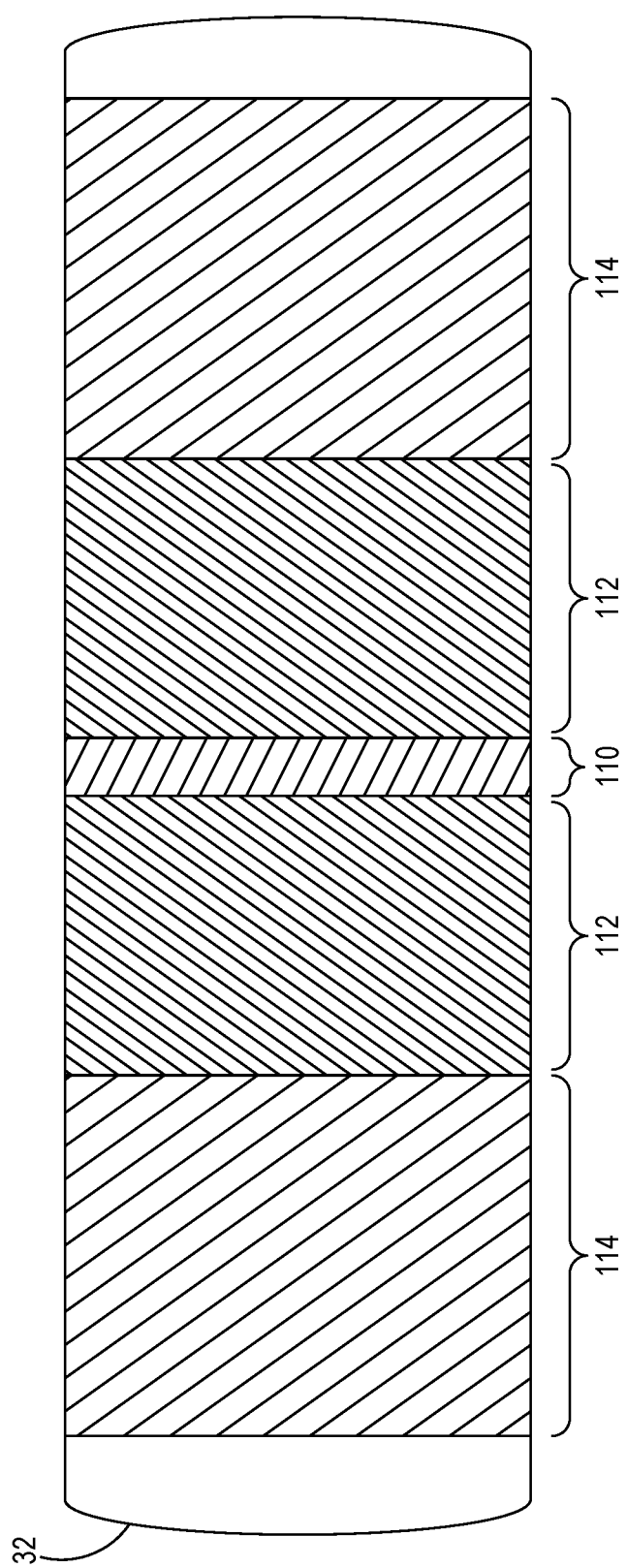
FIG. 13 is a schematic view of a multi-section rotary anvil according to another embodiment.

FIG. 13 illustrates a schematic view of the rotary anvil 32 having mirrored sections such that waist cap anvil portion 110 is bordered on both sides by belly anvil portions 112, which are in turn bordered by leg anvil portions 114. Accordingly, different configurations of the anvil portions corresponding with straight/curved sections of the elastic web 102 are contemplated herein according to the desired design.

As indicated herein, the curved elastic threads 18 such as those illustrated in the leg elastic portion 108 are held in place via ultrasonic bonding, and no adhesive is necessary. Subsequent processing of the elastic web 102 can include cutting the elastic web 102 into discrete sections and also cutting along lines 124 (FIG. 12) to form leg openings and to cut away portions of the elastic threads 18 extending between the first and second leg portions 120, 122.

Therefore, according to one embodiment of the invention, an apparatus for manufacturing an elastic composite structure includes a first roller configured to transport a web layer in a machine direction and a laydown guide configured to guide a laydown pattern of a plurality of elastic threads. A rotary anvil comprises a first weld line having a first notch formed in a contact surface of the first weld line, the first notch having a first interior configured to receive a portion of a first elastic thread of the plurality of elastic threads and a portion of the web layer therein. The first notch comprises a facing surface defining at least a portion of the first interior. A smallest orientation angle of a first face axis normal to the facing surface with respect to a contact surface axis normal to the contact surface is a first angle that is less than 90 degrees.

In accordance with another embodiment of the invention, a bonding apparatus assembly for manufacturing an elastic composite structure comprises a first rotary anvil comprising a first weld line and comprises a second rotary anvil comprising a second weld line. The first weld line includes a first notch formed in a first contact surface of the first weld line, the first notch having a first interior configured to receive a first elastic thread and a first portion of a web layer therein. The first notch comprises a first facing surface defining a portion of the first interior, and a smallest orientation angle of a first face axis normal to the first facing surface with respect to a first contact surface axis normal to a plane of the first contact surface is a first angle that is less than 90 degrees. The second weld line comprises a second notch formed in a second contact surface of the second weld line, the second notch having a second interior configured to receive a second elastic thread and a second portion of the web layer therein. The second notch comprises a second facing surface defining a portion of the second interior, and an orientation angle of a second face axis normal to the second facing surface with respect to a second contact surface axis normal to a plane of the second contact surface is distinct from the smallest orientation angle of the first face axis.

In accordance with another embodiment of the invention, a method for manufacturing an elastic composite structure comprises guiding, in a machine direction, a first web layer adjacently to a rotary anvil via a first roller and guiding an elastic thread adjacently to the rotary anvil via a laydown guide. The rotary anvil comprises a weld line having a notch formed in a contact surface of the weld line, the notch having an interior configured to receive a portion of the elastic thread and a portion of the first web layer therein. The notch comprises a facing surface defining at least a portion of the interior, and a smallest orientation angle of a first face axis normal to the facing surface with respect to a contact surface axis normal to the contact surface is a first angle that is less than 90 degrees.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description but is only limited by the scope of the appended claims.

What is claimed is:

1. An apparatus for manufacturing an elastic composite structure, the apparatus comprising:
   an anvil comprising a face having a first edge and a second edge separated in a cross-machine direction and a first contact surface extending out from the face, the first contact surface including a first notch;
   wherein the first notch has an interior configured to receive a portion of an elastic thread and a portion of a web layer therein;
   wherein the first notch comprises a first facing surface and a second facing surface defining at least a portion of the interior; and
   wherein each of the first facing surface and the second facing surface are in a non-perpendicular orientation relative to the first contact surface and angled toward the first edge of the face.

2. The apparatus of claim 1, wherein the first facing surface and the second facing surface intersect.

3. The apparatus of claim 1, wherein a bottom surface of the notch is curved.

4. The apparatus of claim 1, wherein the first contact surface comprises a pair of land surfaces separated by the first notch.

5. The apparatus of claim 1, wherein the first contact surface defines a portion of a first weld line of the rotary anvil.

6. The apparatus of claim 1 further comprising a plurality of weld lines positioned on the face of the anvil, each weld line of the plurality of weld lines comprising a contact surface and including a first notch having a first interior configured to receive a portion of the elastic thread and a portion of the web layer therein.

7. The apparatus of claim 6 wherein a first notch of one weld line of the plurality of weld lines is wider than a first notch of another weld line of the plurality of weld lines.

8. The apparatus of claim 1 further comprising a first roller configured to transport the web layer in a machine direction.

9. The apparatus of claim 1 further comprising a laydown guide configured to guide a laydown pattern of the elastic thread.

10. The apparatus of claim 1 further comprising an ultrasonic horn.

11. The apparatus of claim 1 further comprising a second contact surface extending out from the face of the anvil, the second contact surface including a second notch; wherein the second notch comprises a first facing surface and a second facing surface defining at least a portion of an interior of the second notch configured to receive a portion of a second elastic thread and a portion of the web layer therein; and wherein the first facing surface and the second facing surface are perpendicular to the second contact surface.

12. An apparatus for manufacturing an elastic composite structure, the apparatus comprising:
- an anvil comprising a first contact surface extending out from a face of the anvil, the first contact surface including a first notch;
- wherein the first notch comprises a first facing surface and a second facing surface defining at least a portion of an interior of the first notch configured to receive a portion of a first elastic thread and a portion of a web layer therein;
- wherein the first facing surface and the second facing surface are angled relative to the first contact surface, with the second facing surface overhanging a portion of the first notch so as to aid in retaining the portion of the first elastic thread within the first notch.

13. The apparatus of claim 12, wherein a bottom surface of the first notch is curved.

14. The apparatus of claim 12, wherein a bottom surface of the first notch is flat.

15. The apparatus of claim 12, wherein the first contact surface comprises a pair of land surfaces separated by the first notch.

16. The apparatus of claim 12 further comprising:
- a first roller configured to transport the web layer in a machine direction; and
- a laydown guide configured to guide a laydown pattern of the first elastic thread.

17. The apparatus of claim 12 further comprising a second contact surface extending out from the face of the anvil, the second contact surface including a second notch;
- wherein the second notch comprises a first facing surface and a second facing surface defining at least a portion of an interior of the second notch configured to receive a portion of a second elastic thread and a portion of the web layer therein; and
- wherein the first facing surface and the second facing surface are perpendicular to the second contact surface.

18. The apparatus of claim 12 further comprising an ultrasonic horn.

19. The apparatus of claim 12 further comprising a plurality of weld lines positioned on the face of the anvil, each weld line of the plurality of weld lines comprising a contact surface and including a first notch having a first interior configured to receive a portion of the elastic thread and a portion of the web layer therein.

20. The apparatus of claim 19 wherein a first notch of one weld line of the plurality of weld lines is wider than a first notch of another weld line of the plurality of weld lines.

* * * * *